US011615535B2

(12) United States Patent
Huo et al.

(10) Patent No.: US 11,615,535 B2
(45) Date of Patent: Mar. 28, 2023

(54) SYSTEMS AND METHODS FOR IMAGE PROCESSING

(71) Applicant: SHANGHAI UNITED IMAGING INTELLIGENCE CO., LTD., Shanghai (CN)

(72) Inventors: Quan Huo, Shanghai (CN); Feng Shi, Shanghai (CN); Qingfeng Li, Shanghai (CN); Bokai Li, Shanghai (CN); Yiqiang Zhan, Shanghai (CN)

(73) Assignee: SHANGHAI UNITED IMAGING INTELLIGENCE CO., LTD., Shanghai (CN)

(*) Notice: Subject to any disclaimer, the term of this patent is extended or adjusted under 35 U.S.C. 154(b) by 0 days.

(21) Appl. No.: 17/457,443

(22) Filed: Dec. 3, 2021

(65) Prior Publication Data
US 2022/0092783 A1 Mar. 24, 2022

Related U.S. Application Data

(63) Continuation of application No. 16/576,264, filed on Sep. 19, 2019, now Pat. No. 11,227,390.

(30) Foreign Application Priority Data

Sep. 26, 2018 (CN) .......................... 201811125405.2
Sep. 26, 2018 (CN) .......................... 201811126495.7

(51) Int. Cl.
*G06T 7/00* (2017.01)
*G06T 7/11* (2017.01)
(Continued)

(52) U.S. Cl.
CPC .............. *G06T 7/0014* (2013.01); *G06T 7/11* (2017.01); *G06T 7/155* (2017.01); *G16H 30/40* (2018.01);
(Continued)

(58) Field of Classification Search
CPC ............................... G16H 50/20; G16H 30/40
See application file for complete search history.

(56) References Cited

U.S. PATENT DOCUMENTS 8,160,357 B2  4/2012  Akinyemi et al.
8,977,029 B2  3/2015  Du et al.
(Continued)

FOREIGN PATENT DOCUMENTS

CN        101615224 A     12/2009
CN        101669828 A      3/2010
(Continued)

OTHER PUBLICATIONS

International Search Report in PCTICN2019/107529 dated Dec. 20, 2019, 4 pages.
(Continued)

*Primary Examiner* — Edward Park
(74) *Attorney, Agent, or Firm* — Metis IP LLC

(57) ABSTRACT

A method for assessing a condition of an organ or tissue of a target object is provided. The method may include: obtaining a target image of the target object; segmenting a target region from the target image, the target region of the target image corresponding to a sub-region of the organ or tissue; determining a morphological characteristic value of the target region in the target image; obtaining a reference standard associated with a sample organ or tissue of a plurality of sample objects, the sample organ or tissue being of a same type as the organ or tissue of the target object; and assessing the condition of the organ or tissue of the target object by comparing the morphological characteristic value of the target region in the target image with the reference standard.

20 Claims, 16 Drawing Sheets

(51) Int. Cl.
  *G06T 7/155* (2017.01)
  *G16H 30/40* (2018.01)
  *G16H 50/20* (2018.01)
(52) U.S. Cl.
  CPC ... *G16H 50/20* (2018.01); *G06T 2207/10072* (2013.01); *G06T 2207/20036* (2013.01); *G06T 2207/20081* (2013.01); *G06T 2207/20084* (2013.01); *G06T 2207/30016* (2013.01)

(56) References Cited

U.S. PATENT DOCUMENTS

| | | | |
|---|---|---|---|
| 9,165,360 | B1 | 10/2015 | Bates et al. |
| 10,185,890 | B2 | 1/2019 | Feiweier et al. |
| 2003/0028401 | A1* | 2/2003 | Kaufman ............... G06Q 10/10 |
| | | | 705/3 |
| 2007/0081699 | A1 | 4/2007 | Avinash et al. |
| 2014/0234810 | A1 | 8/2014 | Flor et al. |
| 2015/0310628 | A1 | 10/2015 | Burry |
| 2015/0335262 | A1 | 11/2015 | George et al. |
| 2015/0356367 | A1 | 12/2015 | Han |
| 2017/0018089 | A1 | 1/2017 | Garnavi et al. |
| 2018/0053297 | A1 | 2/2018 | Celenk et al. |
| 2018/0132725 | A1 | 5/2018 | Vogl et al. |
| 2018/0137623 | A1 | 5/2018 | Stalring |
| 2019/0038239 | A1 | 2/2019 | Flohr et al. |
| 2019/0096060 | A1 | 3/2019 | Zhang et al. |
| 2020/0315455 | A1 | 10/2020 | Lee et al. |

FOREIGN PATENT DOCUMENTS

| | | | |
|---|---|---|---|
| CN | 102999906 | A | 3/2013 |
| CN | 103745227 | A | 4/2014 |
| CN | 105512493 | A | 4/2016 |
| CN | 105913431 | A | 8/2016 |
| CN | 106023220 | A | 10/2016 |
| CN | 106204587 | A | 12/2016 |
| CN | 106295139 | A | 1/2017 |
| CN | 106780512 | A | 5/2017 |
| CN | 107203999 | A | 9/2017 |
| CN | 107516317 | A | 12/2017 |
| CN | 107767376 | A | 3/2018 |
| CN | 108010048 | A | 5/2018 |
| CN | 108231194 | A | 6/2018 |
| CN | 108339614 | A | 8/2018 |
| CN | 106573490 | A | 9/2018 |
| CN | 109242865 | A | 1/2019 |
| CN | 109285152 | A | 1/2019 |
| KR | 101111676 | B1 | 3/2012 |
| WO | 2017091833 | A1 | 6/2017 |

OTHER PUBLICATIONS

Written Opinion in PCT/CN2019/107529 dated Dec. 20, 2019, 5 pages.
John Fox et al., Nonparametric Regression in R: An Appendix to An R Companion to Applied Regression, third edition, 1-17, 2018.
Fausto Milletari et al., V-NET: Fully Convolutional Neural Networks for Volumetric Medical Image Segmentation, 1-11, 2016.
Zheng, Guangyuan et al., Survey on Medical Image Computer Aided Detection and Diagnosis Systems, Journal of Software, 29(5): 1471-1498, 2018.
Nadia Brancati et al., Image Segmentation Via Iterative Histogram Thresholding and Morphological Features Analysis, International Conference Image Analysis and Recognition, 5: 132-141, 2008.
Shi, Yonggang et al., Cascaded Convolutional Neural Network Based Hippocampus Subfields Segmentation, Journal of Image and Graphics, 23(1): 74-83, 2018.
Jonathan Long et al., Fully Convolutional Networks for Semantic Segmentation, 2015 IEEE Conference on Computer Vision and Pattern Recognition (CVPR), 2015, 10 pages.
Notification to Grant Patent for Right for Invention in Chinese Application No. 201811126495.7 dated Aug. 25, 2020, 5 pages.
Mohammad Hesam Hesamian et al., Deep Learning Techniques for Medical Image Segmentation: Achievements and Challenges, Journal of Digital Imaging, 2019, 41 pages.
Guang-Long Wang et al., Morphological Characteristics, Anatomical Structure, and Gene Expression: Novel Insights into Gibberellin Biosynthesis and Perception During Carrot Growth and Development, Horticulture Research, 2: 1-10, 2015.
He, Xiaohai et al., Development and Application for Atlas-Based Brain MRI Images Segmentation Technology, Journal of Data Acquisition and Processing, 30(5): 956-964, 2015.

* cited by examiner

600

601 — Determining at least one percentile value of morphological characteristic values of first sample regions in sample images corresponding to each age, by determining, based on age of the sample object in each sample image, and the morphological characteristic value of the first sample region in each sample image, a ranking of the morphological characteristic values of the first sample regions in the sample images corresponding to each age 603 — Fitting out a curve representing a relation of the morphological characteristic values of the first sample regions in a plurality of sample images and age of the sample objects in the plurality of sample images, by using age as an independent variable, and using the at least one percentile value of morphological characteristic values of first sample regions in sample images corresponding to each age as a dependent variable 605 — Determining a percentile value of the morphological characteristic value of a first target region in a target image among the morphological characteristic values of the first sample regions in a portion of the plurality of sample images, by comparing the age of the target object and the morphological characteristic value of the first target region in the target image with the fitted curve, wherein the sample objects in the portion of the plurality of sample images and the target object are of a substantially same or similar age when the target image and the portion of the plurality of sample images are acquired, respectively 607 — Determining a condition of an organ or tissue of the target object based on the percentile value

FIG. 6

Diagnostic Report

Object Information

| | |
|---|---|
| No. | 00001 |
| Name | Andy |
| Gender | Female |
| Age | 61 |
| Contact Number | 13333333333 |
| Diagnostician | AI |
| Examination Date | 2018.4.24 |

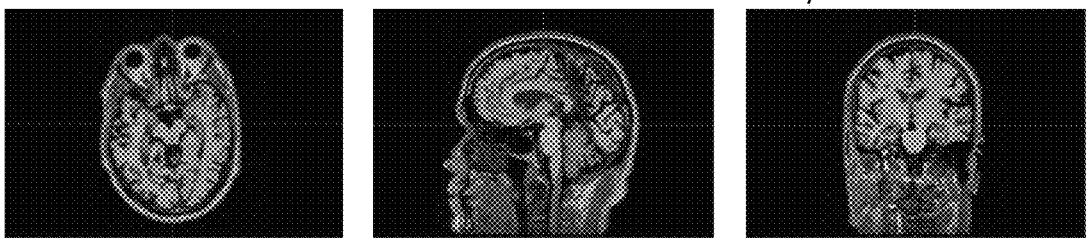

Morphological Characteristic Information

| Sub-region | Volume (1e4) | Percentile | Reference Range |
|---|---|---|---|
| Hippocampus | 1.22 | 3 | (1.13, 1.69) |
| Putamen | 1.16 | 3 | (1.19, 1.79) |
| Anterior Cingulate Cortex | 2.01 | 91 | (1.59, 2.38) |
| Middle Cingulate Cortex | 2.91 | 72 | (2.32, 3.48) |

Comparison with Normal People

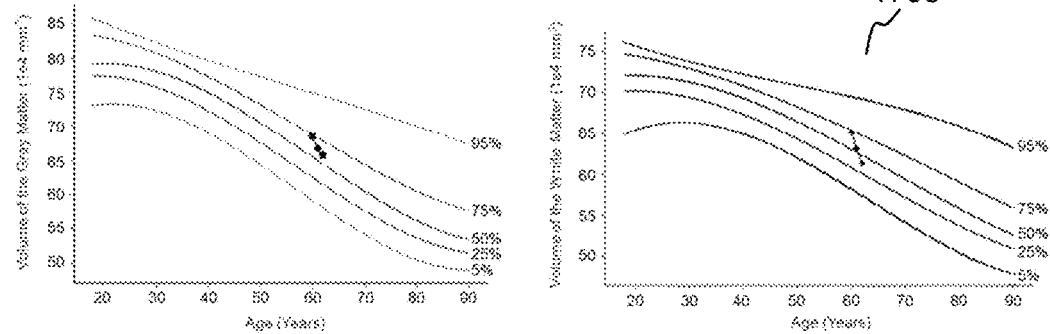

Diagnostic Result

Following 6 regions of the brain of the object indicate brain atrophy: whole brain, gray matter, white matter, amygdala, hippocampus, putamen.

FIG. 17

SYSTEMS AND METHODS FOR IMAGE PROCESSING

CROSS-REFERENCE TO RELATED APPLICATIONS

This application is a Continuation of U.S. patent application Ser. No. 16/576,264, filed on Sep. 19, 2019, which claims priority to Chinese Patent Application No. 201811125405.2, filed on Sep. 26, 2018, and Chinese Patent Application No. 201811126495.7, filed on Sep. 26, 2018, the contents of each of which are incorporated herein by reference.

TECHNICAL FIELD

The present disclosure relates to the field of medical image processing, and in particular, to systems and methods for accessing a condition of an organ or tissue.

BACKGROUND

At present, the proportion of old people of 65 years old and above in China is close to 10%, and China becomes one of the countries with a fast growth rate of aging in the world. The aging process is accompanied by a series of changes in organs or tissues. For example, the function of the brain is mainly manifested by brain atrophy, of which brain images show that the brain tissue structure shrinks, the brain parenchyma decreases, the brain weight decreases, the number (or count) of brain cells decreases, the gyrus flattens, the sulcus broadens and deepens, the ventricle, brain cistern, and subarachnoid space expands, and/or indicate mild gliosis and/or different degrees of cerebral artery degenerative lesions. Exemplary clinical manifestations of brain atrophy include memory deterioration, mood instability, thinking ability decreasing, and/or low attention and concentration. In severe occasions, dementia is developed, and the clinical manifestation includes loss of intelligence. The cause of aging is quite complicated, and has not yet been fully clarified, which has greatly affected the life quality of the old people.

Alzheimer's Disease (AD) is also known as senile dementia. In clinical diagnosis, if a patient's brain atrophies to a certain extent and is diagnosed as AD by scales, the patient mostly has reached an untreatable stage. If early diagnosis of AD is achieved, a conversion from brain atrophy to AD can be delayed by medication.

Traditional brain atrophy assessing and diagnosis of old people is mainly performed according to the following steps: (1) data acquisition, (2) data preprocessing, (3) identification by doctor experience, (4) scale test, and (5) diagnosis. The data acquisition refers to a process of acquiring brain images through an imaging device. The data preprocessing refers to a series of operations (e.g., resampling, orientation adjustment of sampled images, skull removing, gray correction, etc.) for reducing or eliminating the impact of the working condition of the imaging device on the quality of the brain images and providing relatively high quality images for subsequent analysis. The identification by doctor experience refers to that the doctor makes an initial diagnosis, based on the brain images, by observing statuses of the brain atrophy, white matter deformation and/or cerebral infarction. The scale test refers to a cognitive assessment through multi-scales based on a preliminary diagnosis result of the brain images, which is mainly performed through question inquiry and takes about 2-3 hours. Thereafter, a final diagnosis result may be determined based on a combination of a score of the scale test and the preliminary diagnosis result of the brain images.

Traditional methods of the diagnosis of organ or tissue abnormalities (e.g., the brain atrophy) of old people have obtained certain achievements. However, the following problems still exist: first, the diagnosis depends on the doctor's subjective judgment (specifically, descriptions of family members of the patient, cognitive assessment of the patient (e.g., scale test), and the observation of relevant organ or tissue images by the doctor). The method lacks quantitative indicators in diagnosis and is dependent on the doctor's prior knowledge. Second, in the observation and diagnosis of organ or tissue images, even if relevant quantitative morphological characteristics are available, there is no reference standard of normal people of a corresponding age, and the method still relies on experiences of the doctor. At last, with the development of medical devices, the acquisition of organ or tissue images has become more convenient, but quantitative comparison between images of the patient acquired at different times is difficult, and thus the follow-up data of the images cannot be used effectively. Accordingly, it is difficult to analyze a variation trend of the organ or tissue using traditional methods.

Therefore, it is desirable to provide a system, an apparatus and a computer readable storage medium for medical image processing. On the one hand, the systems and methods can quantitatively assess a condition of the organ or tissue of the patient based on images of a corresponding organ or tissue of normal people. On the other hand, the systems and methods can assess the variation trend of the organ or tissue of the patient based on the follow-up data of the organ or tissue images of the patient.

SUMMARY

In the present disclosure, a large number of organ or tissue images of normal people may be acquired. A sub-region may be segmented from these images, and the same sub-region may be segmented from a target image of a target object. The condition of the organ or tissue of the target object may be assessed by comparing a morphological characteristic value of the sub-region of the normal people with that of the sub-region of the target object.

In one aspect of the present disclosure, a method for assessing a condition of an organ or tissue of a target object is provided. The method may include: obtaining a target image of the target object; segmenting a target region from the target image, the target region of the target image corresponding to a sub-region of the organ or tissue; determining a morphological characteristic value of the target region in the target image; obtaining a reference standard associated with a sample organ or tissue of a plurality of sample objects, the sample organ or tissue being of a same type as the organ or tissue of the target object; and/or assessing the condition of the organ or tissue of the target object by comparing the morphological characteristic value of the target region in the target image with the reference standard.

In some embodiments, the target image may be a magnetic resonance (MR) image. In some embodiments, the target object may have an Alzheimer's disease.

In some embodiments, the segmenting a target region from the target image may include: obtaining a target segmentation model; and/or segmenting, using the target segmentation model, the target region from the target image.

In some embodiments, the target segmentation model may include a target artificial intelligence model. In some embodiments, the target artificial intelligence model may include a trained deep learning model.

In some embodiments, the obtaining a target artificial intelligence model may include: retrieving the target artificial intelligence model from a storage device.

In some embodiments, the obtaining a target artificial intelligence model may include: obtaining the target artificial intelligence model by training, using a plurality of training images associated with a second sample organ or tissue of at least one second sample object, an initial artificial intelligence model. The second sample organ or tissue may be of a same type as the organ or tissue of the target object.

In some embodiments, the target artificial intelligence model may be produced according to a process. The process may include: obtaining a plurality of training images associated with a second sample organ or tissue of at least one second sample object, the second sample organ or tissue being of a same type as the organ or tissue of the target object; obtaining an initial artificial intelligence model; and/or determining the target artificial intelligence model by training the initial artificial intelligence model using the plurality of training images.

In some embodiments, the segmenting a target region from the target image may include: segmenting, using a template matching algorithm, the target region from the target image.

In some embodiments, the morphological characteristic value may include at least one of a volume of the organ or tissue, a volume of the target region, a thickness of the target region, and/or a surface area of the target region.

In some embodiments, the organ or tissue may include a brain, and the morphological characteristic value may include at least one of a volume of the brain, a volume of the grey matter of the brain, a volume of the white matter of the brain, a volume of the putamen of the brain, a cortical thickness, or a cortex area.

In some embodiments, the reference standard may relate to a plurality of morphological characteristic values of sample regions in a plurality of sample images of the plurality of sample objects, the sample regions corresponding to the sub-region of the organ or tissue.

In some embodiments, the assessing the condition of the organ or tissue of the target object may include: comparing the morphological characteristic value of the target region with a first portion of the plurality of morphological characteristic values of a first portion of the plurality of sample images corresponding to a first portion of the plurality of sample objects.

In some embodiments, the target object and the first portion of the plurality of sample objects may be of a substantially same or similar age when the target image and the first portion of the plurality of sample images are acquired, respectively. In some embodiments, the target object and the first portion of the plurality of sample objects may be of a same gender.

In some embodiments, the assessing the condition of the organ or tissue of the target object may include: determining a first ranking of the morphological characteristic value of the target region among the first portion of the plurality of morphological characteristic values; and/or assessing the condition of the organ or tissue of the target object based on the first ranking.

In some embodiments, the assessing the condition of the organ or tissue of the target object may include: determining, based on age of the sample object in each of the plurality of sample images when the each sample image is acquired, a second ranking of the morphological characteristic values of the sample regions in the plurality of sample images; determining, based on the second ranking corresponding to the each age, at least one grade of the morphological characteristic values corresponding to the each age; determining, based on the at least one grade, a third ranking of the morphological characteristic value of the target region in the target image among a second portion of the morphological characteristic values of a second portion of the plurality of sample images corresponding to a second portion of the plurality of sample objects; and/or assessing the condition of the organ or tissue of the target object based on the third ranking. The target object and the second portion of the plurality of sample objects may be of a substantially same or similar age when the target image and the second portion of the plurality of sample images are acquired, respectively.

In some embodiments, the assessing the condition of the organ or tissue of the target object may include: determining a relation of the morphological characteristic values corresponding to the plurality of sample objects and age of each of the plurality of sample objects when the each of the plurality of sample images is acquired; and/or determining a grade of the morphological characteristic value corresponding to the target object among a third portion of the morphological characteristic values of a third portion of the plurality of sample images that correspond to a third portion of the plurality of sample objects, based on age of the target object, the morphological characteristic value of the target object, and the relation. The target object and the third portion of the plurality of sample objects may be of a substantially same or similar age when the target image and the third portion of the plurality of sample images are acquired, respectively.

In some embodiments, the determining a relation of the morphological characteristic values corresponding to the plurality of sample objects and age of each of the plurality of sample objects when the each of the plurality of sample images is acquired may include: fitting out a curve representing the relation of the morphological characteristic values corresponding to the plurality of sample objects and the age of the each of the plurality of sample objects when the each of the plurality of sample images is acquired.

In some embodiments, the plurality of morphological characteristic values corresponding to the plurality of sample objects are produced according to a process. The process may include: obtaining the plurality of sample images; for each of the plurality of sample images, segmenting, from the each sample image, a sample region corresponding to the sub-region of the organ or tissue; and/or determining a morphological characteristic value of the sample region in the each sample image.

In some embodiments, the reference standard may include one or more relations relating to a plurality of morphological characteristic values of sample regions in a plurality of sample images of the plurality of sample objects, the sample regions corresponding to the sub-region of the organ or tissue.

In some embodiments, the one or more relations may include at least one first relation associated with one or more sample objects that have a normal condition in the sample organ or tissue.

In some embodiments, the one or more relations may further include at least one second relation associated with one or more sample objects that have an abnormal condition in the sample organ or tissue.

In some embodiments, the one or more relations may be produced according to a process. The process may include: obtaining the plurality of sample images; obtaining age of each of the plurality of sample objects when the each of the plurality of sample images is acquired; segmenting a sample region in each of the plurality of sample images, the sample region being corresponding to the sub-region of the organ or tissue; determining a morphological characteristic value of the sample region in the each sample image; and/or determining a relation between the morphological characteristic values corresponding to the plurality of sample objects and the age of the each of the plurality of sample objects when the each of the plurality of sample images is acquired.

In some embodiments, the method may further include: obtaining a second target image of the target object, the target image and the second target image being acquired at different ages; segmenting, from the second target image, a second target region corresponding to the sub-region of the organ or tissue; determining a second morphological characteristic value of the second target region in the second target image; and/or determining a target variation trend of the morphological characteristic value corresponding to the target object, based on the morphological characteristic value and the second morphological characteristic value corresponding to the target object.

In some embodiments, the method may further include: obtaining a reference variation trend associated with the sample organ or tissue of at least a portion of the plurality of sample objects; and/or assessing the condition of the organ or tissue of the target object by comparing the target variation trend and the reference variation trend.

In another aspect of the present disclosure, a system for assessing a condition of an organ or tissue of a target object is provided. The system may include at least one storage device storing a set of instructions; and/or at least one processor in communication with the storage device. When executing the set of instructions, the at least one processor may be configured to cause the system to perform one or more operations illustrated above.

In another aspect of the present disclosure, a non-transitory computer readable medium storing instructions is provided. The instructions, when executed by at least one processor, may cause the at least one processor to implement the method illustrated above.

In another aspect of the present disclosure, a system for medical image processing is provided. The system may include: a sample data acquisition module configured to acquire a plurality of sample images and age of a sample object in each sample image of the plurality of sample images; a target data acquisition module configured to acquire a target image of a target object and age of the target object; an image segmentation module configured to segment, from the each sample image, a first sample region corresponding to a first sub-region of a sample organ or tissue, and segment, from the target image, a first target region corresponding to a first sub-region of an organ or tissue, the sample organ or tissue being of a same type as the organ or tissue of the target object; a morphological characteristic determination module configured to determine a morphological characteristic value of the first sample region in the each sample image, and determine a morphological characteristic value of the first target region in the target image; and/or an analysis module configured to determine a condition of the organ or tissue of the target object, based on age of each of one or more sample objects in at least one portion of the plurality of sample images, a morphological characteristic value of a first sample region in each one of the at least one portion of the plurality of sample images, the age of the target object, and the morphological characteristic value of the first target region.

In some embodiments, the determination of a condition of the organ or tissue of the target object may include: determining a first ranking of the morphological characteristic value of the first target region among the morphological characteristic values of the first sample regions in a first portion of the plurality of sample images, based on the age of the each of the one or more sample objects in the at least one portion of the plurality of sample images, the morphological characteristic value of the first sample region in the each one of the at least one portion of the plurality of sample images, the age of the target object, and the morphological characteristic value of the first target region; and/or determining, based on the first ranking, the condition of the organ or tissue of the target object. The sample objects in the first portion of the plurality of sample images and the target object may be of a substantially same or similar age when the target image and the first portion of the plurality of sample images are acquired, respectively.

In some embodiments, the determination of a condition of the organ or tissue of the target object may include: determining at least one percentile value of morphological characteristic values of first sample regions in sample images corresponding to each age, by determining, based on age of the sample object in the each sample image when the each sample image is acquired, and the morphological characteristic value of the first sample region in the each sample image, a second ranking of the morphological characteristic values of the first sample regions in the sample images corresponding to the each age; determining, based on the at least one percentile value, a third ranking of the morphological characteristic value of the first target region in the target image among the morphological characteristic values of the first sample regions in a second portion of the plurality of sample images; and/or determining, based on the third ranking, the condition of the organ or tissue of the target object. The sample objects in the second portion of the plurality of sample images and the target object may be of a substantially same or similar age when the target image and the second portion of the plurality of sample images are acquired, respectively.

In some embodiments, the determination of a condition of the organ or tissue of the target object may include: fitting out a curve representing a relation of the morphological characteristic values of the first sample regions in the plurality of sample images and age of the sample objects in the plurality of sample images, by using age as an independent variable, and using at least one percentile value of morphological characteristic values of first sample regions in sample images corresponding to each age as a dependent variable; and/or determining a percentile value of the morphological characteristic value of the first target region in the target image among the morphological characteristic values of the first sample regions in a third portion of the plurality of sample images, by comparing the age of the target object and the morphological characteristic value of the first target region in the target image with the fitted curve. The sample objects in the third portion of the plurality of sample images and the target object may be of a substantially same or similar age when the target image and the third portion of the plurality of sample images are acquired, respectively.

In some embodiments, the sample data acquisition module may be further configured to acquire gender of the sample object in the each sample image. The target data acquisition module may be further configured to acquire gender of the target object. The analysis module may be further configured to determine a fourth ranking of the morphological characteristic value of the first target region in the target image among the morphological characteristic values of the first sample regions in a fourth portion of the plurality of sample images, and/or determine, based on the fourth ranking, the condition of the organ or tissue of the target object. The sample objects in the fourth portion of the plurality of sample images and the target object may be of a substantially same or similar age when the target image and the fourth portion of the plurality of sample images are acquired, respectively.

In some embodiments, the target data acquisition module may be further configured to obtain at least two target images of the target object, the at least two target images being corresponding to different ages when the at least two target images are acquired, respectively. The image segmentation module may be further configured to segment, from each of the at least two target images, a first target region corresponding to the first sub-region of the organ or tissue. The morphological characteristic value determination module may be further configured to determine a morphological characteristic value of the first target region in the each of the at least two target images. The analysis module may be further configured to determine a target variation trend of the morphological characteristic values of the first target regions corresponding to the target object, based on the morphological characteristic values of the first target regions in the at least two target images corresponding to different ages, determine a reference variation trend of a morphological characteristic value of a first sample region corresponding to the first sub-region of the organ or tissue, based on age corresponding to each of a fifth portion of the plurality of sample images, and the morphological characteristic value of the first sample region in the each of the fifth portion of the plurality of sample images, and/or determine the condition of the organ or tissue in the target image of the target object by comparing the target variation trend and the reference variation trend.

In some embodiments, the image segmentation module may be further configured to segment, from the each sample image, a second sample region corresponding to a second sub-region of the organ or tissue, and/or segment, from the target image, a second target region corresponding to the second sub-region of the organ or tissue. The morphological characteristic determination module may be further configured to determine a morphological characteristic value of the second sample region in the each sample image, and/or determine a morphological characteristic value of the second target region in the target image. The analysis module may be further configured to determine the condition of the organ or tissue of the target object, based on age of the sample object in the each sample image when the each sample image is acquired, the morphological characteristic value of the second sample region in the each sample image, the age of the target object, and the morphological characteristic value of the second target region in the target image.

In some embodiments, the image segmentation module may be further configured to segment, using a deep learning model and/or a template matching algorithm, the first sample region from the each sample image, and/or the first target region from the target image.

BRIEF DESCRIPTION OF THE DRAWINGS

The present disclosure is further described in detail of exemplary embodiments. These exemplary embodiments are described in detail with reference to the drawings. These embodiments are not limiting, and in these embodiments, the same number indicates the same structure, wherein:

FIG. 6 is a flowchart illustrating an exemplary process for determining a ranking of a morphological characteristic value associated with a sub-region (e.g., the first sub-region) of an organ or tissue of a target object among morphological characteristic values associated with the sub-region of the organ or tissue of sample objects that are of the same age as the target object according to some embodiments of the present disclosure;

FIG. 17 is a schematic diagram of an exemplary diagnostic report according to some embodiments of the present disclosure.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof. It will be understood that the term "object" and "subject" may be used interchangeably as a reference to a thing that undergoes a treatment and/or an imaging procedure in a radiation system of the present disclosure.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

Figure 2:
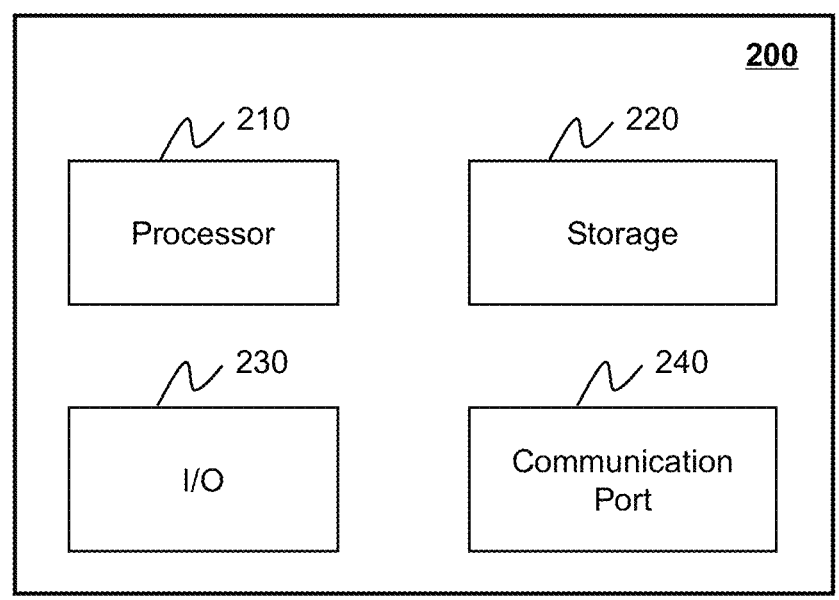
FIG. 2 is a schematic diagram illustrating an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may apply to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood the operations of the flowcharts may be implemented not in order. Conversely, the operations may be implemented in inverted order, or simultaneously. Moreover, one or more other operations may be added to the flowcharts. One or more operations may be removed from the flowcharts.

The present disclosure relates to systems and methods for assessing a condition of an organ or tissue of a target object. The systems and methods may obtain a target image of the target object. The systems and methods may segment a target region from the target image. The target region of the target image may correspond to a sub-region of the organ or tissue. The systems and methods may determine a morphological characteristic value of the target region in the target image. The systems and methods may also obtain a reference standard associated with a sample organ or tissue of a plurality of sample objects. The sample organ or tissue may be of the same type as the organ or tissue of the target object. The systems and methods may assess the condition of the organ or tissue of the target object by comparing the morphological characteristic value of the target region in the target image with the reference standard.

According to the systems and methods of the present disclosure: (1) a three-dimensional Convolutional Neural Network (3D CNN) may be used for segmenting brain sub-structures to obtain morphological characteristic values of brain sub-regions; (2) a medical image may be divided into one or more sub-regions, and a condition of an organ or tissue of a target object may be comprehensively assessed by comparing morphological characteristic values of the sub-regions; (3) a risk degree of the organ or tissue of the target object may be quantified by comparing morphological characteristic value(s) of the organ or tissue of the target object with morphological characteristic value(s) of a corresponding organ or tissue of normal people; (4) a target variation trend of morphological characteristic values of the organ or tissue of the target object may be determined according to follow-up data of the target object, and the risk degree of the organ or tissue of the target object may be determined by comparing the target variation trend of the target object with a reference variation trend of normal people. It should be noted that different embodiments may have different beneficial effects. The beneficial effects of different embodiments may be any combination of one or more of the beneficial effects mentioned above. In some embodiments, any other beneficial effect not mentioned in the present disclosure may also be obtained.

It should be understood that application scenarios of systems and methods disclosed herein are only some exemplary embodiments provided for the purposes of illustration, and not intended to limit the scope of the present disclosure. For persons having ordinary skills in the art, multiple variations and modifications may be made under the teachings of the present disclosure.

Figure 1:
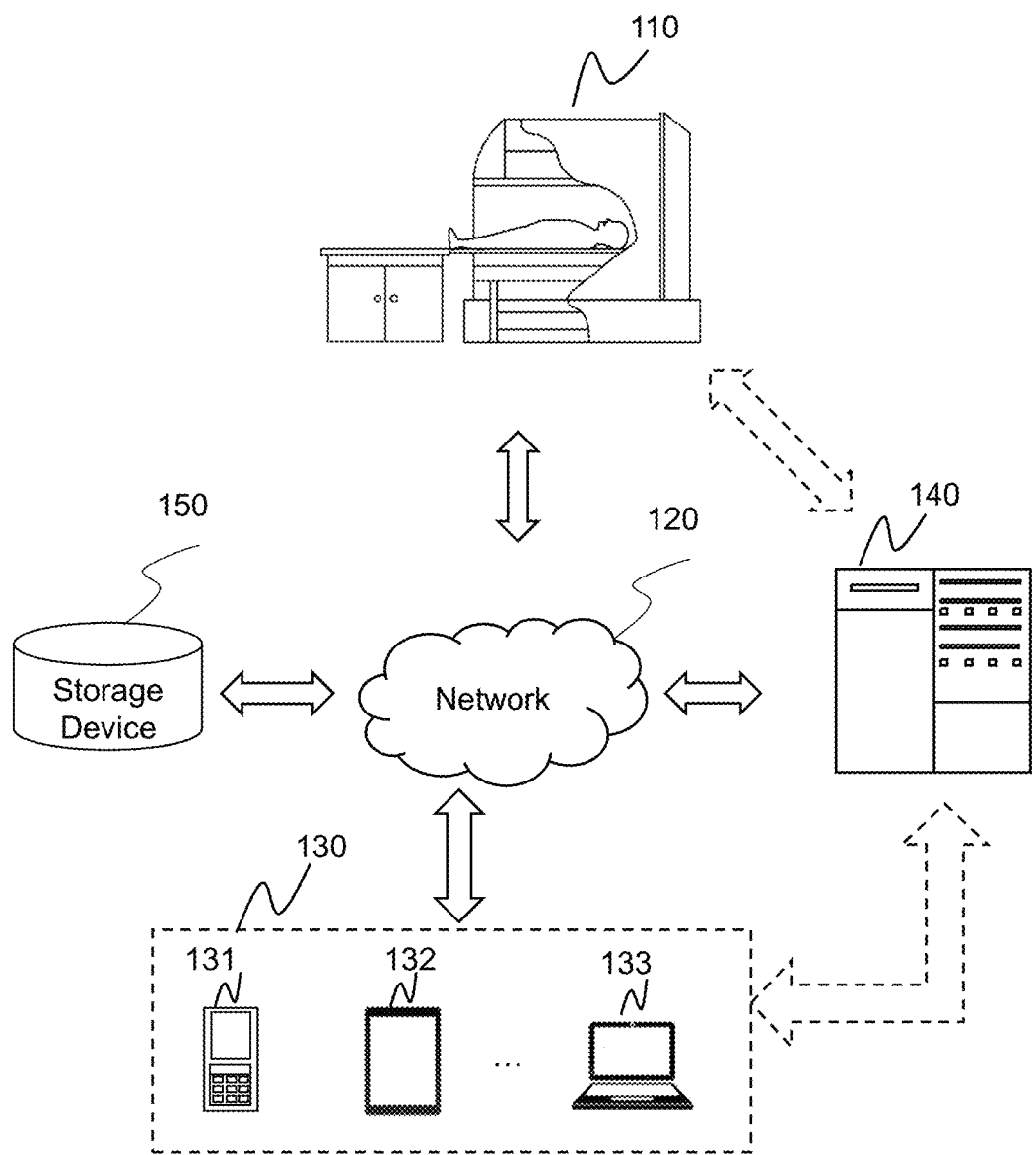
FIG. 1 is a schematic diagram illustrating an exemplary application scenario of an image processing system according to some embodiments of the present disclosure.

FIG. 1 is a schematic diagram illustrating an exemplary application scenario of an image processing system according to some embodiments of the present disclosure. As shown in FIG. 1, the image processing system 100 may include a scanner 110, a network 120, one or more terminals 130, a processing device 140, and a storage device 150.

The components in the image processing system 100 may be connected in one or more of various ways. Merely by way of example, the scanner 110 may be connected to the processing device 140 through the network 120. As another example, the scanner 110 may be connected to the processing device 140 directly as indicated by the bi-directional arrow in dotted lines linking the scanner 110 and the processing device 140. As still another example, the storage device 150 may be connected to the processing device 140 directly or through the network 120. As a further example, the terminal 130 may be connected to the processing device 140 directly (as indicated by the bi-directional arrow in dotted lines linking the terminal 130 and the processing device 140) or through the network 120.

The scanner 110 may scan a subject that is located within its detection region to obtain image data of the subject. The scanned subject may be a part of an organ or tissue of a human body, such as the head of the human body. In some embodiments, the scanner 110 may be a Magnetic Resonance (MR) scanner. The MR scanner may include a magnet (e.g., a superconducting magnet), a gradient coil, a radio frequency (RF) coil, etc. (not shown in FIG. 1). In some embodiments, the MR scanner may be a closed-bore scanner, an open-bore scanner, or the like.

In some embodiments, the subject may be biological or non-biological. Merely by way of example, the subject may include a patient, an organ, a tissue, a specimen, a man-made object, a phantom, etc. In some embodiments, the subject to be scanned (also referred to as imaged) may include a body, substance, or the like, or any combination thereof. In some embodiments, the subject may include a specific portion of a body, such as a head, a thorax, an abdomen, or the like, or any combination thereof. In some embodiments, the subject may include a specific organ, such as a breast, an esophagus, a trachea, a bronchus, a stomach, a gallbladder, a small intestine, a colon, a bladder, a ureter, a uterus, a fallopian tube, etc. In the present disclosure, "object" and "subject" are used interchangeably.

In some embodiments, the scanner 110 may include a Computed Tomography (CT) scanner, a Positron Emission Tomography (PET) scanner, a Single-Photon Emission Computed Tomography (SPECT) scanner, an ultrasonography scanner, a Digital Radiography (DR) scanner, or the like, or any combination thereof.

The network 120 may include any suitable network that can facilitate the image processing system 100 to exchange information and/or data. In some embodiments, one or more of components (e.g., the scanner 110, the terminal(s) 130, the processing device 140, the storage device 150, etc.) of the image processing system 100 may communicate information and/or data with one another via the network 120. For example, the processing device 140 may acquire image data from the scanner 110 via the network 120. As another example, the processing device 140 may obtain user instructions from the terminal(s) 130 via the network 120. The network 120 may be and/or include a public network (e.g., the Internet), a private network (e.g., a local area network (LAN), a wide area network (WAN), etc.), a wired network (e.g., an Ethernet), a wireless network (e.g., an 802.11 network, a Wi-Fi network, etc.), a cellular network (e.g., a Long Term Evolution (LTE) network), an image relay network, a virtual private network ("VPN"), a satellite network, a telephone network, a router, a hub, a switch, a server computer, and/or a combination of one or more thereof. For example, the network 120 may include a cable network, a wired network, a fiber network, a telecommunication network, a local area network, a wireless local area network (WLAN), a metropolitan area network (MAN), a public switched telephone network (PSTN), a Bluetooth™ network, a ZigBee™ network, a near field communication network (NFC), or the like, or a combination thereof. In some embodiments, the network 120 may include one or more network access points. For example, the network 120 may include wired and/or wireless network access points, such as base stations and/or network switching points, through which one or more components of the image processing system 100 may access the network 120 for data and/or information exchange.

In some embodiments, a user (e.g., a doctor, or an operator) may operate the image processing system 100 through the terminal(s) 130. The terminal(s) 130 may include a mobile device 131, a tablet computer 132, a laptop computer 133, or the like, or a combination thereof. In some embodiments, the mobile device 131 may include a smart home device, a wearable device, a mobile device, a virtual reality device, an augmented reality device, or the like. In some embodiments, the smart home device may include a smart lighting device, a control device of an intelligent electrical apparatus, a smart monitoring device, a smart television, a smart video camera, an interphone, or the like, or a combination thereof. In some embodiments, the wearable device may include a bracelet, footgear, glasses, a helmet, a watch, clothing, a backpack, a smart accessory, or the like, or a combination thereof. In some embodiments, the mobile device may include a mobile phone, a personal digital assistant (PDA), a gaming device, a navigation device, a point of sale (POS) device, a laptop, a tablet computer, a desktop, or the like, or a combination thereof. In some embodiments, the virtual reality device and/or augmented reality device may include a virtual reality helmet, virtual reality glasses, a virtual reality eyewear, an augmented reality helmet, augmented reality glasses, an augmented reality eyewear, or the like, or a combination thereof. For example, the virtual reality device and/or augmented reality device may include a Google Glass™, an Oculus Rift™, a Hololens™, a Gear VR™, or the like. In some embodiments, the terminal(s) 130 may be part of the processing device 140.

The processing device 140 may process data and/or information obtained from the scanner 110, the terminal(s) 130, and/or the storage device 150. For example, the processing device 140 may process a target image to assess the condition of an organ or tissue of a target object. In some embodiments, the processing device 140 may be a server or a server group. The server group may be centralized or distributed. In some embodiments, the processing device 140 may be local or remote. For example, the processing device 140 may access information and/or data stored in the scanner 110, the terminal(s) 130, and/or the storage device 150 via the network 120. As another example, the processing device 140 may be directly connected to the scanner 110, the terminal(s) 130, and/or the storage device 150 to access stored information and/or data. In some embodiments, the processing device 140 may be implemented on a cloud platform. For example, the cloud platform may include a private cloud, a public cloud, a hybrid cloud, a community cloud, a distributed cloud, an interconnected cloud, a multiple cloud, or the like, or a combination thereof. In some embodiments, the processing device 140 may be implemented by a computing device 200 having one or more components as described in FIG. 2.

In some embodiments, the processing device 140 may process data and/or information obtained from an external resource. For example, the processing device 140 may obtain a target segmentation model from a third party (e.g., an external storage device of a medical institution, a public service organization, or a medical company) that provides the target segmentation model via the network 120. The processing device 140 may segment a target region from a target image using the target segmentation model. In some embodiments, the processing device 140, or a portion of the processing device 140 may be integrated into the scanner 110.

The storage device 150 may store data, instructions, and/or any other information. In some embodiments, the storage device 150 may store data obtained from the terminal(s) 130, the scanner 110, and/or the processing device 140. In some embodiments, the storage device 150 may store data and/or instructions that the processing device 140 may execute or use to perform exemplary methods described in the present disclosure. In some embodiments, the storage device 150 may include a mass storage device, a removable storage device, a volatile read-and-write memory, a read-only memory (ROM), or the like. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be executed on a cloud platform. For example, the cloud platform may include a private cloud, a public cloud, a hybrid cloud, a community cloud, a distributed cloud, an interconnected cloud, a multiple cloud, or the like, or a combination thereof.

In some embodiments, the storage device 150 may be connected to the network 120 to communicate with one or more other components (e.g., the processing device 140, the terminal(s) 130, etc.) of the image processing system 100. One or more components of the image processing system 100 may access data or instructions stored in the storage device 150 via the network 120. In some embodiments, the storage device 150 may be directly connected to or communicate with one or more other components (e.g., the processing device 140, the terminal(s) 130, etc.) of the image processing system 100. In some embodiments, the storage device 150 may be part of the processing device 140.

FIG. 2 is a schematic diagram illustrating an exemplary computing device according to some embodiments of the present disclosure. The computing device 200 may be used to implement any component of the image processing system 100 as described herein. For example, the processing device 140 and/or the terminal(s) 130 may be implemented on the computing device 200, respectively, via its hardware, software program, firmware, or a combination thereof. Although only one such computing device is shown, for convenience, the computer functions relating to the image processing system 100 as described herein may be implemented in a distributed manner on a number of similar platforms, to distribute the processing load.

As shown in FIG. 2, the computing device 200 may include a processor 210, a storage 220, an input/output (I/O) 230, and a communication port 240.

The processor 210 may execute computer instructions (e.g., program code) and perform functions of the image processing system 100 (e.g., the processing device 140) in accordance with techniques described herein. The computer instructions may include, for example, routines, programs, objects, components, data structures, procedures, modules, and functions, which perform particular functions described herein. For example, the processor 210 may process image data obtained from any components of the image processing system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or a combination thereof.

Merely for illustration, only one processor is described in the computing device 200. However, it should be noted that the computing device 200 in the present disclosure may also include multiple processors, thus operations and/or method operations that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from any components of the image processing system 100. In some embodiments, the storage 220 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. The removable storage device may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc.

In some embodiments, the storage 220 may store one or more programs and/or instructions to perform exemplary methods described in the present disclosure. For example, the storage 220 may store a program for the processing device 140 to assess a condition of an organ or tissue of a target object.

The I/O 230 may input and/or output signals, data, information, etc. In some embodiments, the I/O 230 may enable user interaction with the image processing system 100 (e.g., the processing device 140). In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network to facilitate data communications. The communication port 240 may establish connections between the processing device 140 and the scanner 110, the terminal(s) 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or a combination thereof. The wireless connection may include a Bluetooth™ link, a Wi-Fi™ link, a WiMax™ link, a WLAN link, a ZigBee™ link, a mobile network link (e.g., 3G, 4G, 5G), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
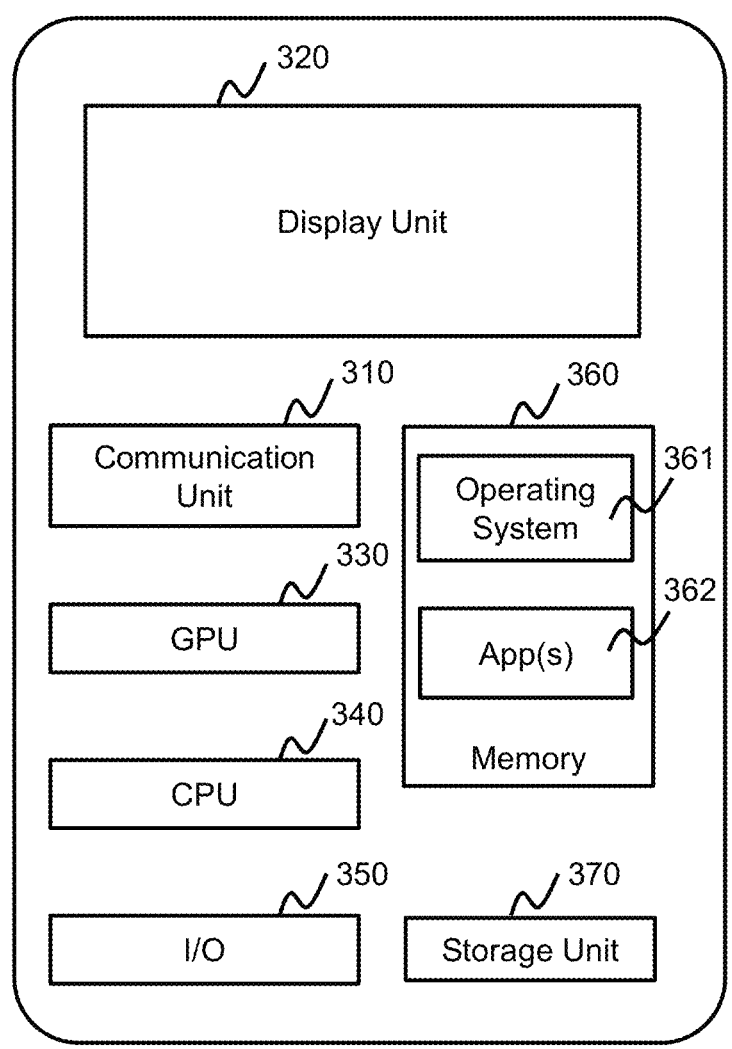
FIG. 3 is a block diagram illustrating an exemplary mobile device on which the terminal(s) may be implemented according to some embodiments of the present disclosure.

FIG. 3 is a block diagram illustrating an exemplary mobile device on which the terminal(s) 130 may be implemented according to some embodiments of the present disclosure.

As shown in FIG. 3, the mobile device 300 may include a communication unit 310, a display unit 320, a graphics processing unit (GPU) 330, a central processing unit (CPU) 340, an I/O 350, a memory 360, a storage unit 370, etc. In some embodiments, any other suitable component, including but not limited to a system bus or a controller (not shown), may also be included in the mobile device 300. In some embodiments, an operating system 361 (e.g., iOS™, Android™, Windows Phone™, etc.) and one or more applications (apps) 362 may be loaded into the memory 360 from the storage unit 370 in order to be executed by the CPU 340. The application(s) 362 may include a browser or any other suitable mobile apps for receiving and rendering information relating to imaging, image processing, or other information from the image processing system 100 (e.g., the processing device 140). User interactions with the information stream may be achieved via the I/O 350 and provided to the processing device 140 and/or other components of the image processing system 100 via the network 120. In some embodiments, a user may input parameters to the image processing system 100, via the mobile device 300.

In order to implement various modules, units and their functions described above, a computer hardware platform may be used as hardware platforms of one or more elements (e.g., the processing device 140 and/or other components of the image processing system 100 described in FIG. 1). Since these hardware elements, operating systems and program languages are common; it may be assumed that persons skilled in the art may be familiar with these techniques and they may be able to provide information needed in the imaging and assessing according to the techniques described in the present disclosure. A computer with the user interface may be used as a personal computer (PC), or other types of workstations or terminal devices. After being properly programmed, a computer with the user interface may be used as a server. It may be considered that those skilled in the art may also be familiar with such structures, programs, or general operations of this type of computing device.

FIGS. 4A-4D are schematic diagrams illustrating exemplary processing devices according to some embodiments of the present disclosure.

Figure 4A:
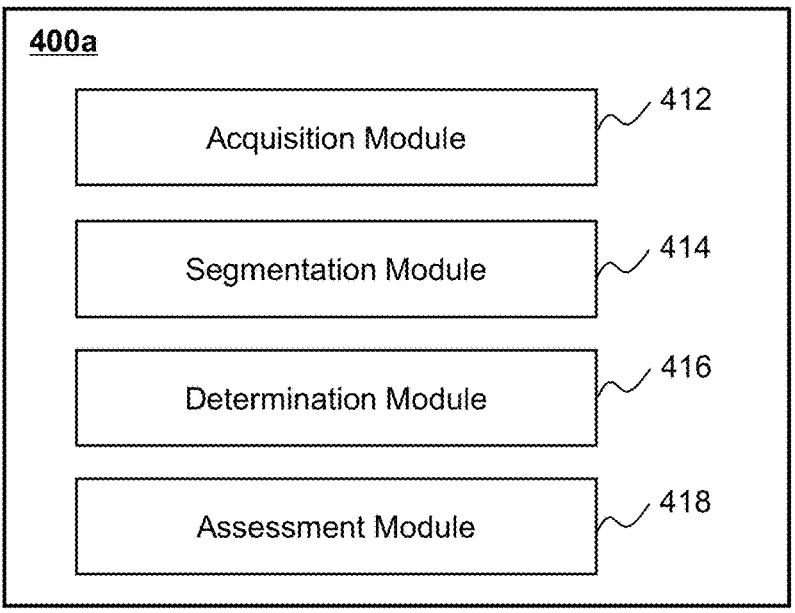
FIGS. 4A-4D are schematic diagrams illustrating exemplary processing devices according to some embodiments of the present disclosure.

As shown in FIG. 4A, the processing device 400a may include an acquisition module 412, a segmentation module 414, a determination module 416, and an assessment module 418.

The acquisition module 412 may be configured to obtain information and/or data from one or more components associated with the image processing system 100. For example, the acquisition module 412 may obtain one or more images (e.g., a target image of a target object). As another example, the acquisition module 412 may obtain a reference standard associated with a sample organ or tissue of a plurality of sample objects. More descriptions regarding the target image and the reference standard may be found elsewhere in the present disclosure (e.g., FIG. 5A and the descriptions thereof).

The segmentation module 414 may be configured to segment one or more images (e.g., the target image). In some embodiments, the segmentation module 414 may segment a target region from the target image. For example, the segmentation module 414 may segment the target region using a target segmentation model. More descriptions regarding the segmentation of the target region and the target segmentation model 414 may be found elsewhere in the present disclosure (e.g., FIG. 5A and the descriptions thereof).

The determination module 416 may be configured to determine morphological characteristic values associated with an object (e.g., the target object). In some embodiments, the determination module 416 may determine a morphological characteristic value of the target region in the target image of the target object. More descriptions regarding the determination of the morphological characteristic value may be found elsewhere in the present disclosure (e.g., FIG. 5A and the descriptions thereof).

The assessment module 418 may be configured to assess a condition of an organ or tissue (e.g., of the target object). In some embodiments, the assessment module 418 may assess the condition based on the morphological characteristic value of the target region in the target image and/or the reference standard. Merely by way of example, the assessment module 418 may assess the condition of the organ or tissue of the target object by comparing the morphological characteristic value of the target region in the target image with the reference standard. More descriptions regarding the assessment may be found elsewhere in the present disclosure (e.g., FIG. 5A and the descriptions thereof).

Figure 4B:
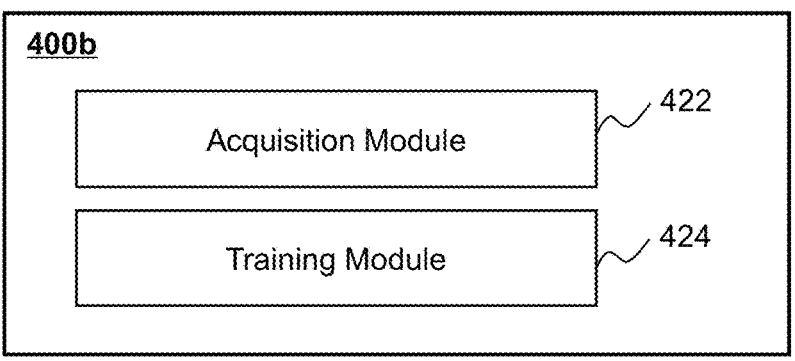

As shown in FIG. 4B, the processing device 400b may include an acquisition module 422 and a training module 424.

The acquisition module 422 may be configured to obtain one or more images (e.g., a plurality of training images). In some embodiments, the acquisition module 422 may obtain the plurality of training images from a storage device (e.g., the storage device 150, the storage 220, the storage unit 370, or an external storage device (e.g., in a hospital or a medical institution) that can communicate with the image processing system 100 (e.g., via the network 120)). More descriptions regarding the training images may be found elsewhere in the present disclosure (e.g., FIG. 5B and the descriptions thereof). The acquisition module 422 may be configured to obtain an initial artificial intelligence model. In some embodiments, the acquisition module 422 may obtain the initial artificial intelligence model from a storage device (e.g., the storage device 150, the storage 220, the storage unit 370, or an external storage device (e.g., in a hospital or a medical institution) that can communicate with the image processing system 100 (e.g., via the network 120)). More descriptions regarding the initial artificial intelligence model may be found elsewhere in the present disclosure (e.g., FIG. 5B and the descriptions thereof).

The training module 424 may be configured to train a model (e.g., the initial artificial intelligence model). For example, the training module 424 may train the initial artificial intelligence model using the plurality of training images to generate a trained artificial intelligence model. More descriptions regarding the training process may be found elsewhere in the present disclosure (e.g., FIG. 5B and the descriptions thereof).

Figure 4C:
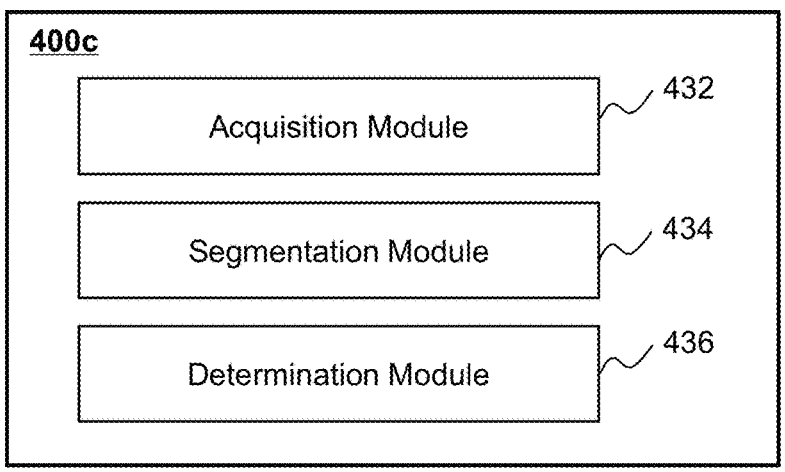

As shown in FIG. 4C, the processing device 400c may include an acquisition module 432, a segmentation module 434, and a determination module 436.

The acquisition module 432 may be configured to obtain one or more images (e.g., a plurality of sample images of a plurality of sample objects). In some embodiments, the acquisition module 432 may obtain age of an object (e.g., age of each of the plurality of sample objects when each of the plurality of sample images is acquired). More descriptions regarding the sample images and the age of each of the plurality of sample objects may be found elsewhere in the present disclosure (e.g., FIG. 5C and the description thereof).

The segmentation module 434 may be configured to segment an image (e.g., each of the plurality of sample images). For example, the segmentation module 434 may segment a sample region in each of the plurality of sample images. More descriptions regarding the segmentation of the sample region may be found elsewhere in the present disclosure (e.g., FIG. 5C and the description thereof).

The determination module 436 may be configured to determine a morphological characteristic value associated with an object (e.g., a morphological characteristic value of the sample region in each sample image). In some embodiments, the determination module 436 may determine a relation between the morphological characteristic values corresponding to the plurality of sample objects and age of each of the plurality of sample objects when each of the plurality of sample images is acquired. More descriptions regarding the determination of the morphological characteristic value and the relation may be found elsewhere in the present disclosure (e.g., FIG. 5C and the description thereof).

Figure 4D:
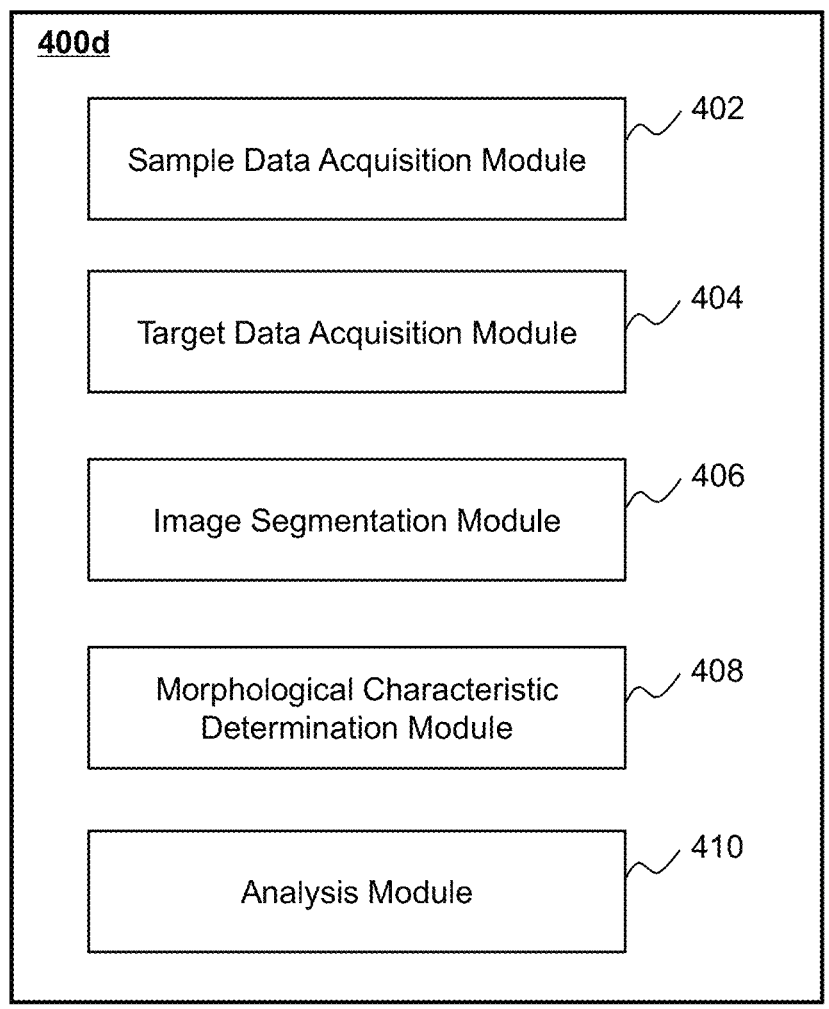

FIG. 4D is a schematic diagram illustrating another exemplary processing device according to some embodiments of the present disclosure. In some embodiments, the processing device 400d may include a sample data acquisition module 402, a target data acquisition module 404, an image segmentation module 406, a morphological characteristic determination module 408, and an analysis module 410.

The sample data acquisition module 402 may be configured to acquire sample data. The sample data may include sample images. In some embodiments, the sample data acquisition module 402 may acquire a plurality of sets of sample data including a plurality of sample images. In some embodiments, the plurality of sample images may include three-dimensional (3D) images and/or two-dimensional (2D) images. In some embodiments, the plurality of sample images may include images of at least one organ or tissue. Exemplary organs may include but not limited to a brain, a lung, a heart, a kidney, a liver, etc. Exemplary tissues may include but not limited to epithelial tissues, connective tissues, nervous tissues, muscular tissues, etc. In some embodiments, the plurality of sample images may be of a same modality or different modalities, e.g., MR images, CT images, PET-CT images, PET-MR images, etc. In some embodiments, the plurality of sample images may be of different types of a same modality. Taking brain MR sample images as an example, the brain MR sample images may include but not limited to a T1-weighted image, a T2-weighted image, a Fluid-attenuated inversion recovery (FLAIR) image, etc., of the brain. The sample data acquisition module 402 may also acquire age of a sample object in each sample image. In some embodiments, the age may be an integer age, such as 50 years old, 60 years old, 61 years old, or the like. In some embodiments, the age may be accurate to at least one decimal place, such as 60.1 years old, 60.5 years old, or the like. In some embodiments, the sample data acquisition module 402 may also acquire gender of the sample object in each sample image.

The target data acquisition module 404 may be configured to acquire target data including one or more target images of the target object and/or age of the target object. The target image may be an image of an organ or tissue. In some embodiments, if the plurality of sample images are associated with a same organ or tissue, the target image may also be associated with the same organ or tissue. In some embodiments, if the plurality of sample images are associated with different organs or tissues, the organ or tissue in the target image may be the same as an organ or tissue in at least part of the sample images. For example, the sample images may be associated with at least two of the organs (including the brain, a lung, the heart, a kidney, the liver, etc.), and the target image may be associated with any one of the at least two organs. In some embodiments, if the plurality of sample images are of a same modality, the target image may be of the same modality. In some embodiments, if the plurality of sample images are of different modalities, the target image may be of a modality that is the same as that of at least part of the sample images. For example, the sample images may be of at least two modalities including MR, CT, PET-CT, PET-MR, or the like, and the target image may be of any one of the at least two modalities. In some embodiments, the target data acquisition module 404 may acquire follow-up data of the target object. The follow-up data may include a plurality of target images of the target object. The target images may be collected at different ages of the target object. In some embodiments, the target data acquisition module 404 may also obtain gender of the target object.

The image segmentation module 406 may be configured to segment an image into at least one region corresponding to a sub-region of an organ or tissue. For example, an organ may include different portions (or sub-regions). In some embodiments, the image segmentation module 406 may segment an organ image into at least one region corresponding to a sub-region of the organ or tissue according to the portions of the organ. The image segmentation module 404 may segment the image using at least one image segmentation algorithm. Exemplary image segmentation algorithms may include but not limited to a deep learning model, a template matching algorithm, or the like. In some embodiments, the deep learning model may be a 3D CNN. The 3D CNN may be used to process image(s) of an entire organ or tissue. The template matching algorithm may include a single template matching algorithm, a multi-template matching algorithm, or the like.

Figure 8:
FIG. 8 is an exemplary transverse image illustrating brain sub-regions segmented from a brain image according to some embodiments of the present disclosure.
Figure 9:
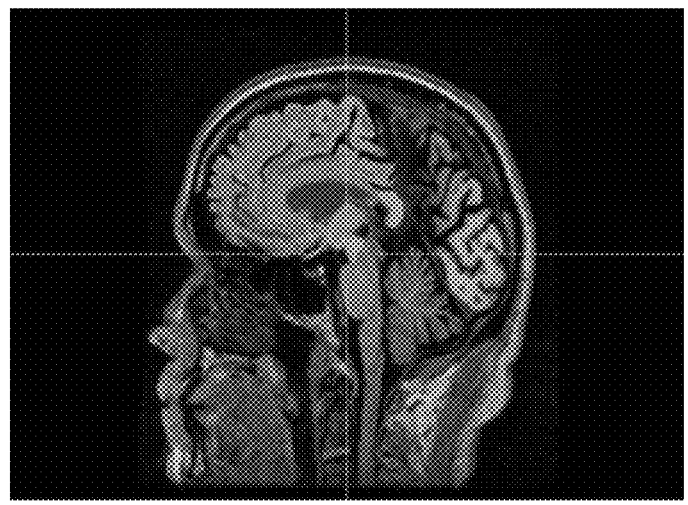
FIG. 9 is an exemplary sagittal image illustrating brain sub-regions segmented from a brain image according to some embodiments of the present disclosure.
Figure 10:
FIG. 10 is an exemplary coronal image illustrating brain sub-regions segmented from a brain image according to some embodiments of the present disclosure.

Taking a brain image as an example, in some embodiments, the image segmentation module 406 may segment the brain image into a plurality of regions corresponding to brain sub-regions. Exemplary brain sub-regions may include the whole brain, the grey matter, the white matter, the amygdala, the putamen, the hippocampus, the globus pallidus, the thalamus, the anterior cingulate cortex, the middle cingulate cortex, the posterior cingulate cortex, the insula, the superior temporal gyrus, the middle temporal gyrus, the temporal pole, etc. FIGS. 8-10 are schematic diagrams of a plurality of brain sub-regions segmented from a brain image, in which FIG. 8 illustrates a transverse image, FIG. 9 illustrates a sagittal image, and FIG. 10 illustrates a coronal image.

The morphological characteristic determination module 408 may be configured to determine a morphological characteristic value of a sub-region of an organ or tissue. In some embodiments, the morphological characteristic value of a sub-region may be determined using at least one morphometry technique. Exemplary morphometry techniques may include a voxel-based morphometry technique, a tensor-based morphometry technique, a deformation-based morphometry technique, or the like. Taking a brain image as an example, morphological characteristics of the brain image may include but not limited to a volume, a cortical thickness, a cortex area, a gyrification index, or the like.

The analysis module 410 may be configured to determine a condition of an organ or tissue of the target object according to the sample data and/or the target data In some embodiments, the analysis module 410 may determine the condition of the organ or tissue of the target object according to age of a sample object in each of at least one portion of the sample images, a morphological characteristic value of a specific sample region (corresponding to a specific sub-region of the organ or tissue) in each of the at least one portion of the sample images, the age of the target object, and/or a morphological characteristic value of a target region (corresponding to a target sub-region of the organ or tissue) in the target image. In some embodiments, the analysis module 410 may determine a ranking of the morphological characteristic value of the target region of the target image among morphological characteristic values of the specific sample regions of a portion of the plurality of sample images, and determine the condition of the organ or tissue of the target object based on the ranking. In some embodiments, the sample objects in the portion of the plurality of sample images and the target object are of a substantially same or similar age when the target image and the portion of the plurality of sample images are acquired, respectively.

In the present disclosure, a sample object is of a substantially same or similar age as the target object refers to that the sample object and the target object are of a substantially same or similar age when the target image associated with the target object and the sample image(s) associated with the sample object are acquired, respectively. A sample object is of a same gender as the target object refers to that the sample object and the target object are of a same gender when the target image associated with the target object and the sample image(s) associated with the sample object are acquired, respectively.

In some embodiments, the analysis module 410 may rank the morphological characteristic values of specific sample regions in the sample images corresponding to each age, based on age of the sample object in each sample image, and the morphological characteristic value of the specific sample region in each sample image, and/or determine at least one percentile value of morphological characteristic values of the specific sample regions in sample images corresponding to each age. In some embodiments, the analysis module 410 may fit out a curve representing a relation of the morphological characteristic values of the specific sample regions in a plurality of sample images and age of each of the sample objects in the plurality of sample images, e.g., by using age as an independent variable, and using the at least one percentile value of morphological characteristic values of the specific sample regions in sample images corresponding to each age as a dependent variable. In some embodiments, the analysis module 410 may determine a percentile value of the morphological characteristic value of the target region in the target image among the morphological characteristic values of the specific sample regions in a portion of the plurality of sample images, by comparing the age of the target object and the morphological characteristic value of the target region in the target image with the fitted curve. In some embodiments, the sample objects in the portion of the plurality of sample images and the target object may be of a substantially same or similar age when the target image and the portion of the plurality of sample images are acquired, respectively. More descriptions regarding the determination of the percentile value of the target object among the sample objects of the same age as the target object based on the fitted curve may be found elsewhere in the present disclosure (e.g., FIG. 6 and descriptions thereof).

In some embodiments, the analysis module 410 may further determine a ranking of the morphological characteristic value of the target region of the target image among morphological characteristic values of the specific sample regions of a portion of the sample images, and/or determine the condition of the organ or tissue of the target object according to the ranking. In some embodiments, the sample objects in the portion of the sample images and the target object may be of a substantially same or similar age when the target image and the portion of the sample images are acquired, respectively. In some embodiments, the sample objects in the portion of the sample images and the target object may be of a same gender. In some embodiments, the analysis module 410 may determine a target variation trend of morphological characteristic values of the target region of the target image based on the follow-up data of the target object; determine a reference variation trend of a morphological characteristic value of the specific sample region based on the sample images and/or the age of each of sample objects in the sample images; and/or compare the target variation trend with the reference variation trend to determine the condition of the organ or tissue of the target object. More descriptions regarding the determination of the condition of the organ or tissue of the target object may be found elsewhere in the present disclosure (e.g., FIGS. 7 and 12-14 and descriptions thereof).

It may be understood that the processing device 400d illustrated above may be used to assess the condition of the organ or tissue of the target object, thereby assisting a doctor in making diagnosis, and improving the diagnosis efficiency. In some embodiments, the processing device 400d itself may not directly output a diagnostic result.

It should be noted that the above description of modules of the processing device is merely provided for the purposes of illustration, and not intended to limit the present disclosure. For persons having ordinary skills in the art, the modules may be combined in various ways or connected with other modules as sub-systems under the teaching of the present disclosure and without departing from the principle of the present disclosure. For example, in some embodiments, the sample data acquisition module 402, the target data acquisition module 404, the image segmentation module 406, the morphological characteristic determination module 408, and the analysis module 410 may be different modules in a processing device, or may be a module that implements functions of two or more modules mentioned above. In some embodiments, the principle of the present disclosure may be applied to other image processing systems.

As illustrated above, processing devices 400a-400d may be exemplary configurations of the processing device 140. In some embodiments, the processing devices 400a-400d may share one or more of the modules illustrated above. For instance, the processing devices 400a-400d may be part of a same system and share a same acquisition module. For example, the acquisition modules 412, 422, and 432 may be a same module. In some embodiments, the processing devices 400a-400d may be different devices belonging to different parties. For example, the processing device 400b may belong to a manufacturer of the scanner 110 or a medical company and may be configured to train a target segmentation model offline. As another example, the processing device 400a may belong to a hospital or a medical company and may be configured to use the trained segmentation model to assess the organ or tissue of the target object online. As a further example, the processing device 400c may belong to a hospital, a manufacturer of the scanner 110, or a medical company, or the like.

Figure 5A:
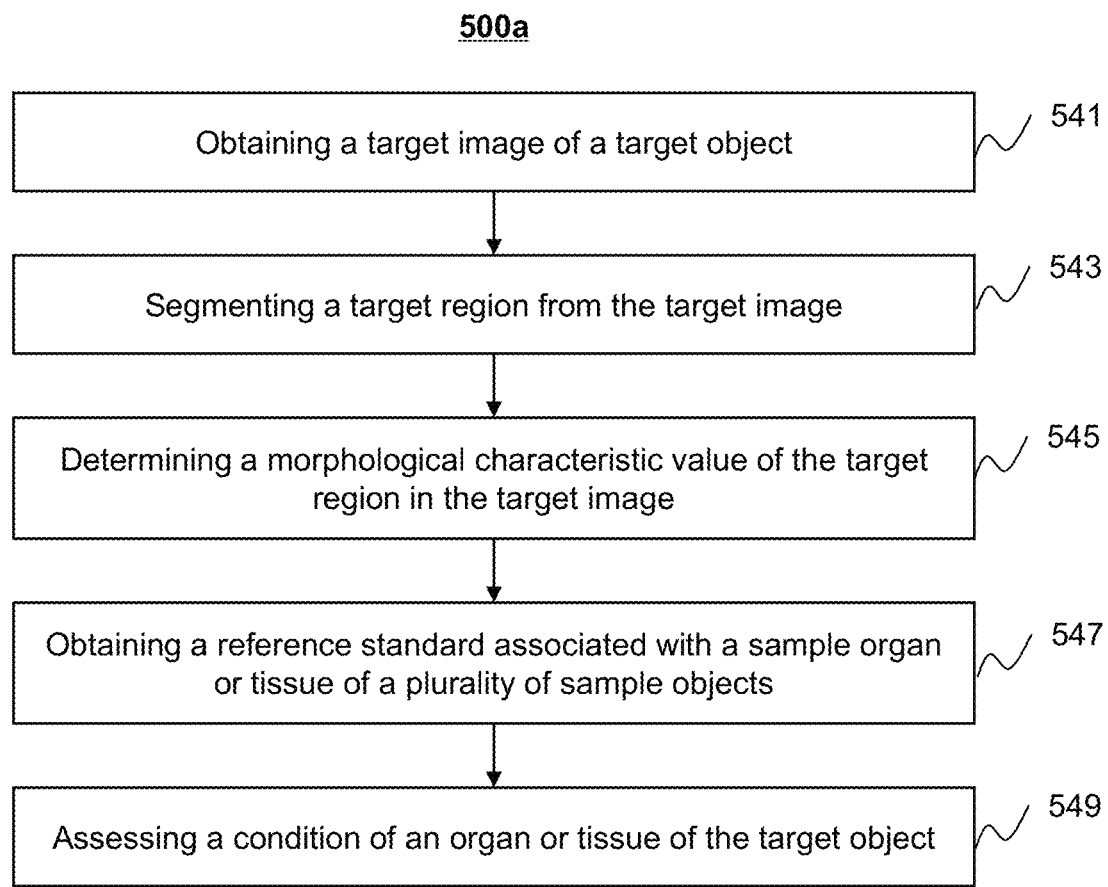
FIG. 5A is a flowchart illustrating an exemplary process for assessing a condition of an organ or tissue of a target object according to some embodiments of the present disclosure.

FIG. 5A is a flowchart illustrating an exemplary process for assessing a condition of an organ or tissue of a target object according to some embodiments of the present disclosure. In some embodiments, process 500a may be executed by the image processing system 100. For example, the process 500a may be implemented as a set of instructions (e.g., an application) stored in a storage device (e.g., the storage device 150, the storage 220, and/or the storage unit 370). In some embodiments, the processing device 140 (e.g., the processor 210 of the computing device 200, the CPU 340 of the mobile device 300, and/or one or more modules illustrated in FIGS. 4A-4D) may execute the set of instructions and may accordingly be directed to perform the process 500a.

Figure 5B:
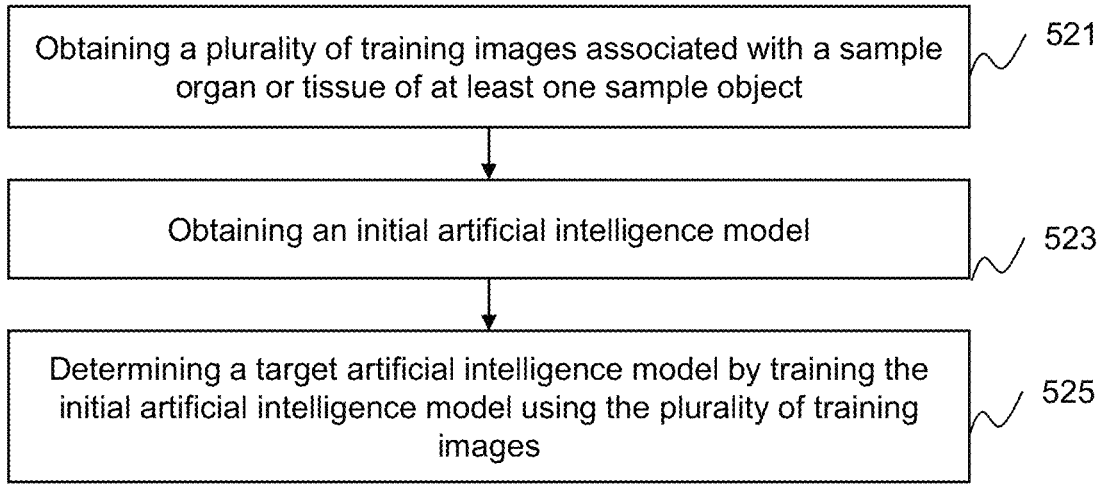
FIG. 5B is a flowchart illustrating an exemplary process for determining a target artificial intelligence model according to some embodiments of the present disclosure.
Figure 5C:
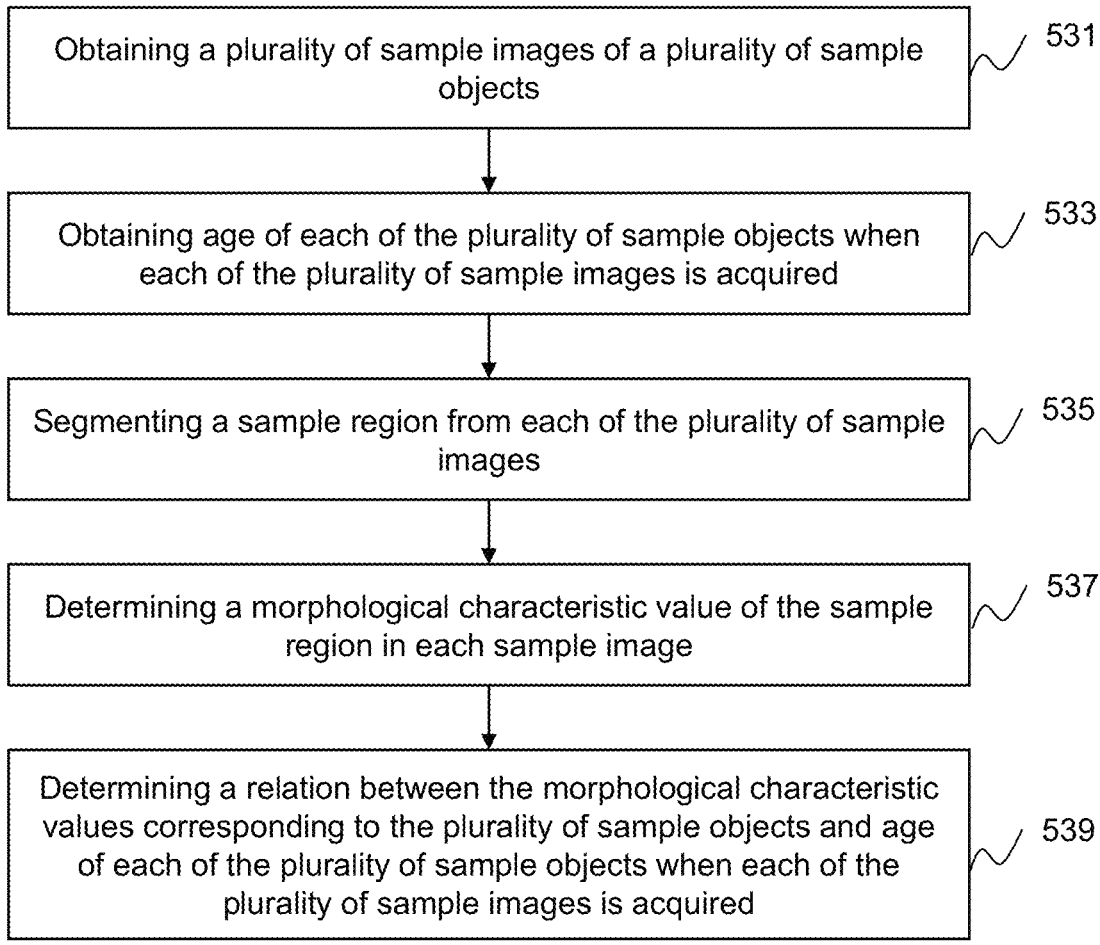
FIG. 5C is a flowchart illustrating an exemplary process for determining a relation between morphological characteristic values corresponding to a plurality of sample objects and age of each of the plurality of sample objects when each of a plurality of sample images is acquired according to some embodiments of the present disclosure.
Figure 5D:
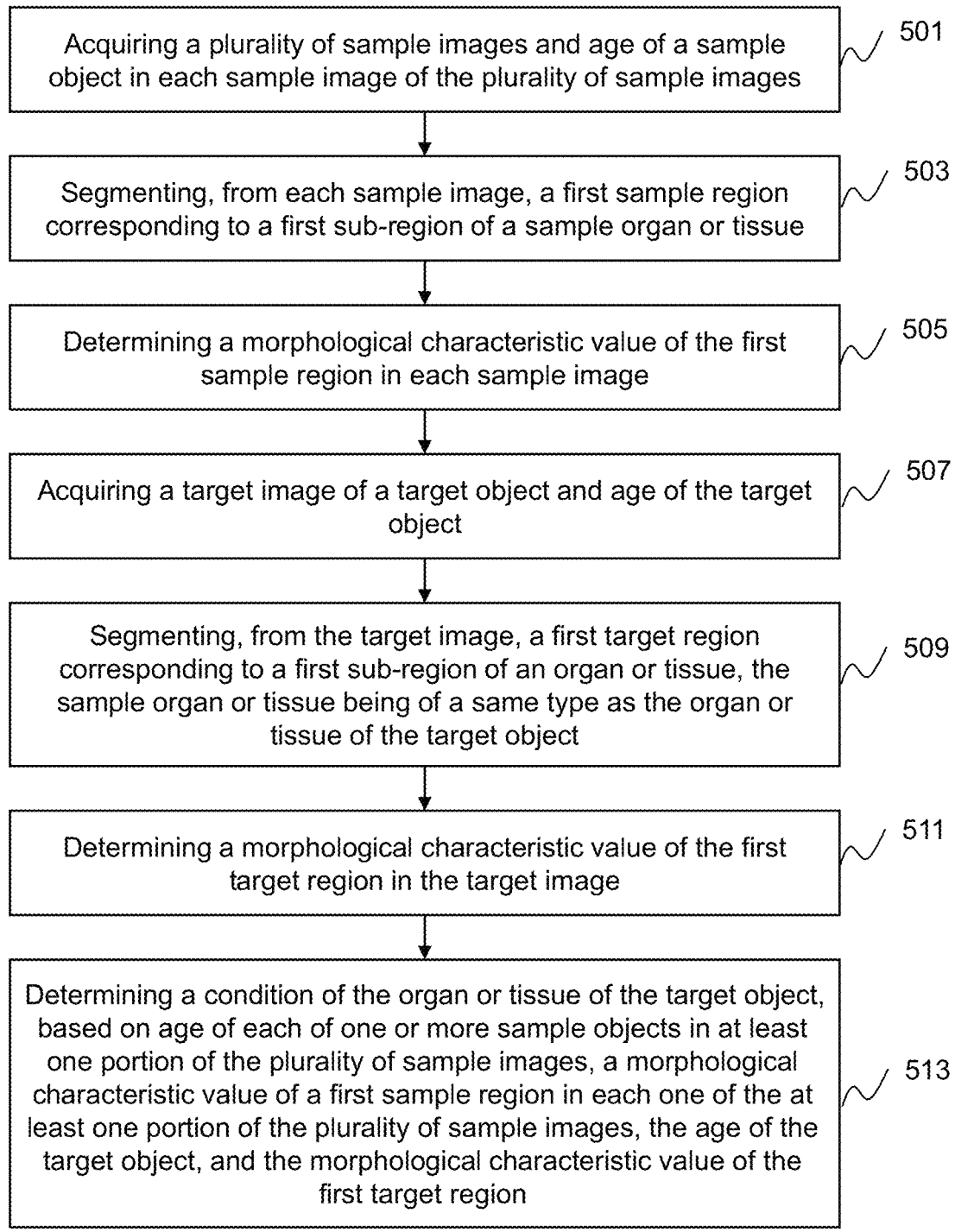
FIG. 5D is a flowchart illustrating an exemplary medical image processing process according to some embodiments of the present disclosure.

In 541, the processing device 400a (e.g., the acquisition module 412) may obtain a target image of the target object (see, e.g., operation 507 in FIG. 5D and the descriptions thereof).

In some embodiments, the target object may be a patient or a potential patient that has a disease (or disorder) in an organ or tissue. Exemplary organ diseases may include a brain disease (e.g., a central nervous system (CNS) disorder), a lung disease, a heart disease, a kidney disease, a liver disease, a spleen disease, etc. Exemplary CNS disorders may include a Alzheimer's Disease (AD), a Idiopathic Parkinson's disease, a Mild Cognitive Impairment (MCI), a Vascular Dementia (VaD), a Cerebral Amyloid Angiopathy (CAA), a Frontotemporal Lobar Degeneration (FTLD), a Dementia with Lewy Bodies (DLB), a Progressive Supranuclear Palsy (PSP), a Multiple System Atrophy (MSA), a Creutzfeldt-Jakob Disease (CJD), a Traumatic Brain Injury, or the like. Exemplary tissue disorders may include a tendon disease, a ligamentous injury, a bone bruise, a joint disease, a muscle injury, a meniscus injury, etc. In some embodiments, the target object may be a person that is to be tested whether s/he has a disease in an organ (or tissue) or not.

The target image may refer to an image that is associated with an organ or tissue of the target object. Exemplary organs or tissues may include the brain, a lung, the heart, a kidney, the liver, the spleen, epithelial tissues, connective tissues, nervous tissues, muscular tissues, or the like. In some embodiments, the target image may be of a modality, e.g., an MR image, a CT image, a PET image, a PET-CT image, a PET-MR image, or the like. In some embodiments, the target image may be of a type of a specific modality. Taking a brain MR image as an example, the target image may be a T1-weighted image, a T2-weighted image, a T2*-weighted image, a FLAIR image, or the like, of the brain of the target object. The target image may be a two-dimensional (2D) image or a three-dimensional (3D) image. If the target image is a 3D image, the target image may be represented by a plurality of 2D images (e.g., slice images) relating to the organ or tissue of the target object.

In some embodiments, the processing device 400a may obtain the target image from one or more components of the image processing system 100. For example, the target image may be reconstructed based on image data collected by the scanner 110 and/or be stored in the storage device 150. The processing device 400a may retrieve and/or obtain the target image from the storage device 150.

In 543, the processing device 400a (e.g., the segmentation module 414) may segment a target region from the target image (see, e.g., operation 509 in FIG. 5D and the descriptions thereof).

The target region may correspond to a sub-region of an organ or tissue of the target object. In some embodiments, the sub-region of the organ or tissue may be associated with the disease. In some embodiments, statuses or variations of the sub-region of the organ or tissue may indicate whether the target object has the disease or the target object's risk degree of disease. Taking the brain as an example, the sub-region of the brain may include the whole brain, the grey matter, the white matter, the amygdala, the putamen, the hippocampus, the globus pallidus, the thalamus, the cingulate cortex (e.g., the anterior cingulate cortex, the middle cingulate cortex, or the posterior cingulate cortex), the insula, the superior temporal gyrus, the middle temporal gyrus, the temporal pole, the praecuneus, the parietal lobe, the temporal lobe, the gyrus, the sulcus, the cingulate sulcus (e.g., the posterior cingulate sulcus), the parietooccipital sulcus, the choroid fissure, the entorhinal cortex, the corpus callosum, the whole-brain cortex, the temporoparietal cortex, the ventricle, the brain cistern, etc. Exemplary brain sub-regions segmented from a brain image may be shown in, e.g., FIGS. 8-10.

As used herein, a representation of an object (e.g., a patient, or a portion thereof) in an image may be referred to the object for brevity. For instance, a representation of an organ or tissue (e.g., the heart, the liver, a lung, etc., of a patient) in an image may be referred to as the organ or tissue for brevity. As used herein, an operation on a representation of an object in an image may be referred to as an operation on the object for brevity. For instance, a segmentation of a portion of an image including a representation of an organ or tissue (e.g., the heart, the liver, a lung, etc., of a patient) from the image may be referred to as a segmentation of the organ or tissue for brevity.

It should be noted that the target region may be a 2D region or a 3D volume. If the target region is a 3D volume, the target region may be represented by a plurality of 2D regions.

In some embodiments, the processing device 400*a* may obtain a target segmentation model, and segment the target region from the target image using the target segmentation model. In some embodiments, the target image may be input to the target segmentation model, and the target segmentation model may output the target region. In some embodiments, the target segmentation model may be used to segment images of different modalities, e.g., MR images, CT images, PET images, PET-CT images, PET-MR images, etc. In some embodiments, the target segmentation model may identify a modality of the target image, and segment the target image. The target segmentation model may automatically segment the target image in a relative short time (e.g., 0.2 seconds, 0.5 seconds). In some embodiments, the target segmentation model may include a template matching model (e.g., a single template matching algorithm, or a multi-template matching algorithm). In some embodiments, the target segmentation model may include a target artificial intelligence model, such as a trained deep learning model (e.g., a trained 3D CNN model). In some embodiments, the target artificial intelligence model may be determined by training an initial artificial intelligence model using a plurality of training images associated with a sample organ or tissue of at least one sample object. For example, the target artificial intelligence model may be trained by the processing device 400*b*. The processing device 400*b* may store the target artificial intelligence model in a storage device (e.g., the storage device 150, the storage 220, the storage unit 370). As another example, the target artificial intelligence model may be trained in an external device, and stored in a storage device (e.g., the storage device 150, the storage 220, the storage unit 370, or an external storage device that can communicate with the image processing system 100 (e.g., via the network 120)). The processing device 400*a* (e.g., the acquisition model 412) may retrieve the target artificial intelligence model from the storage device. In some embodiments, the processing device 400*a* may train the target artificial intelligence model online. More descriptions regarding the determination of the target artificial intelligence model may be found elsewhere in the present disclosure (e.g., FIG. 5B and the descriptions thereof).

In 545, the processing device 400*a* (e.g., the determination module 416) may determine a morphological characteristic value of the target region in the target image (see, e.g., operation 511 in FIG. 5D and the descriptions thereof).

The morphological characteristic value of the target region may include a volume of an organ or tissue, a volume of the target region, a density of the target region, a thickness of the target region, a surface area of the target region, a width of the target region, a deformation (size and/or orientation) of the target region, etc. In some embodiments, the processing device 400*a* may determine the morphological characteristic value of the target region using one or more morphometry techniques. Exemplary morphometry techniques may include a voxel-based morphometry technique, a tensor-based morphometry technique, a deformation-based morphometry technique, or the like, or any combination thereof. Merely by way of example, the volume of the target object, the density of the target region, the thickness of the target region, the surface area of the target region, the width of the target region and the density of the object may be determined using the voxel-based morphometry technique and/or the tensor-based morphometry technique. The deformation of the target object may be determined using the deformation-based morphometry technique.

Taking the brain as an example, exemplary morphological characteristic values of the target region of the brain may include a volume of the brain (e.g., a Total Intracranial Volume (TIV)), a volume of the gray matter, a volume of the white matter, a volume of the putamen, a volume of the gyrus, a volume of the hippocampus, a volume of the temporal lobe, a volume of the praecuneus, a volume of the entorhinal cortex, a volume of the corpus callosum, a volume of the temporoparietal cortex, a cortical thickness of the brain (e.g., a thickness of the entorhinal cortex, a thickness of the temporoparietal cortex), a cortex area of the brain (e.g., a surface area of the whole brain cortex, a surface area of the entorhinal cortex, a surface area of the temporoparietal cortex), a width of the choroid fissure, a width of the cingulate sulcus, a width of the parietooccipital sulcus, or the like.

In 547, the processing device 400*a* (e.g., the acquisition module 412) may obtain a reference standard associated with a sample organ or tissue of a plurality of sample objects. The sample organ or tissue may be of a same type as the organ or tissue of the target object.

The reference standard may relate to a plurality of morphological characteristic values of sample regions in a plurality of sample images of the plurality of sample objects. The sample regions may correspond to the sub-region of the organ or tissue. In some embodiments, the processing device 400*a* may obtain the plurality of sample images. For each of the plurality of sample images, the processing device 400*a* may segment a sample region corresponding to the sub-region of the organ or tissue from each sample image. The processing device 400*a* may determine a morphological characteristic value of the sample region in each sample image. In some embodiments, the plurality of morphological characteristic values corresponding to the plurality of sample objects may be produced in an external device (e.g., an external device that can provide the reference standard). The external device may determine the reference standard based on the plurality of morphological characteristic values corresponding to the plurality of sample objects. Thus, the reference standard may be determined based on the plurality of morphological characteristic values corresponding to the plurality of sample objects.

In some embodiments, the sample objects may include normal people. The normal people may refer to people of which a sample organ or tissue of interest (e.g., the brain) is in a normal condition at his/her age when a corresponding sample image is collected. A sample organ or tissue may refer to an organ or tissue of a sample object. If the sample objects include normal people, the reference standard may indicate a normal level or variation of morphological characteristic values of normal people, and a condition of the target region of the target object may be assessed by comparing the morphological characteristic value of the target region with the reference standard.

In some embodiments, the sample objects may include abnormal people. The abnormal people may refer to people of which a sample organ or tissue of interest (e.g., the brain) is in an abnormal condition at his/her age when a corresponding sample image is collected. If the sample objects include abnormal people, the reference standard may indicate an abnormal level or variation of morphological characteristic values of abnormal people. If the condition of the organ or tissue of the target object is assessed to be at a risk, a severity of the disease of the target object may be further assessed or verified by comparing the morphological characteristic value of the target region with the reference standard associated with abnormal people.

In some embodiments, the sample objects may be of various ages or age ranges. In some embodiments, the sample objects may be of one or more races. In some embodiments, the sample objects may have one or more disease labels. In some embodiments, different sample objects may have different disease labels.

In some embodiments, the reference standard may include one or more relations relating to the plurality of morphological characteristic values of sample regions in the plurality of sample images of the plurality of sample objects. The one or more relations may include at least one first relation associated with one or more sample objects that have a normal condition in the sample organ or tissue, at least one second relation associated with one or more sample objects that have an abnormal condition in the sample organ or tissue. The normal condition may refer to that the sample object(s) do not have a disease in the corresponding sample organ or tissue. The abnormal condition may refer to that the sample object(s) have a disease in the corresponding sample organ or tissue. Taking the brain as an example, the normal condition may refer to that the sample object(s) have a healthy brain without any brain disease, and the abnormal condition may refer to that the sample object(s) have an unhealthy brain with one or more brain diseases described elsewhere in the present disclosure. In some embodiments, the first relation(s) may be used to determine a certain risk degree (e.g., a relatively high risk, a medium risk, a relatively low risk) of a certain disease that the target object may have. The second relation(s) may be used to determine a particular type or severity of disease that the target object may have. For example, if the target object is determined to have a relatively high risk of a CNS disorder based on the first relation(s), the target object may be determined to have a particular type of the CNS disorder based on the second relation(s). In some embodiments, the one or more relations may be produced in an external device. More descriptions regarding the determination of the one or more relations may be found elsewhere in the present disclosure (e.g., FIGS. 5C, 6 and 7 and the descriptions thereof).

In some embodiments, the processing device 400a may obtain the reference standard from a storage device (e.g., the storage device 150, the storage 220, the storage unit 370, a public database, a non-public database, or an external storage device that can communicate with the image processing system 100 (e.g., via the network 120)). For example, the reference standard may be produced by the processing device 400b, processing device 400c, or a third party (e.g., a medical institution for providing the reference standard), and be stored in the storage device. The processing device 400a may retrieve the reference standard from the storage device.

In 549, the processing device 400a (e.g., the assessment module 418) may assess the condition of the organ or tissue of the target object.

Figure 11:
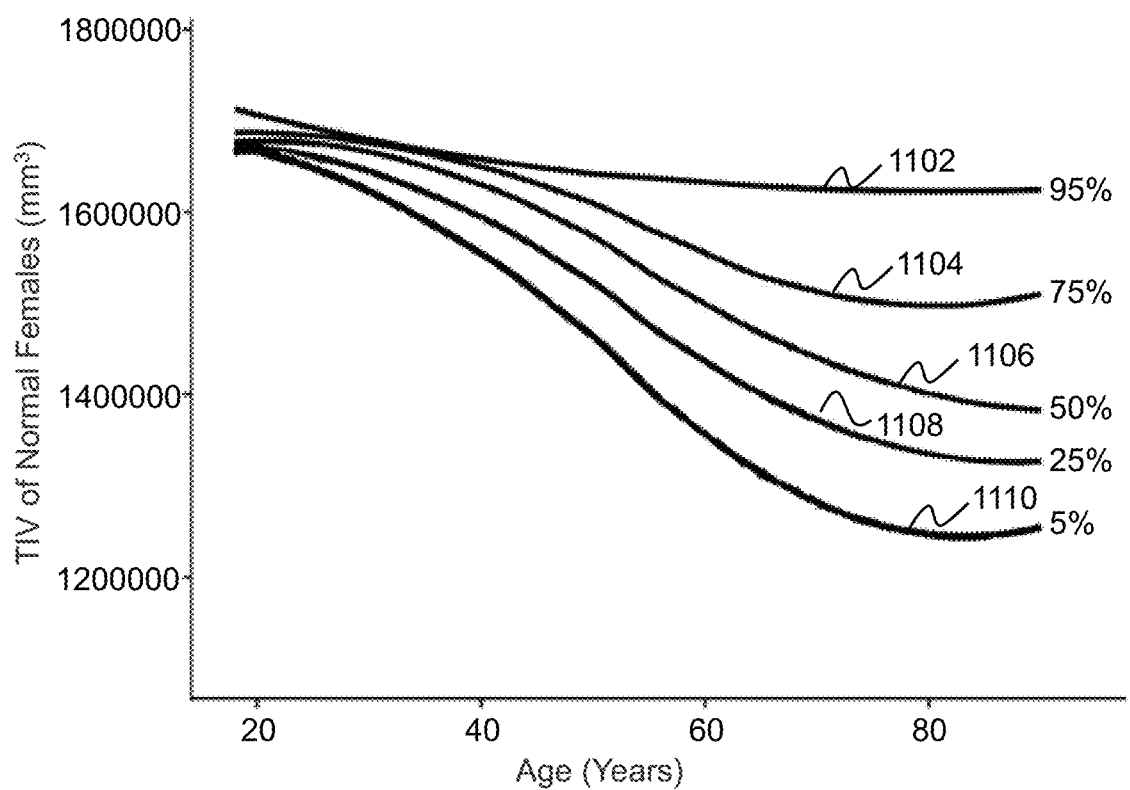
FIG. 11 is a schematic diagram illustrating exemplary curves representing a relation of percentile values of TIVs of normal females and ages of the normal females according to some embodiments of the present disclosure.

In some embodiments, the processing device 400a may assess the condition of the organ or tissue of the target object by comparing the morphological characteristic value of the target region in the target image with the reference standard (see, e.g., curves in FIG. 11). For example, the processing device 400a may compare the morphological characteristic value of the target region with a portion of the plurality of morphological characteristic values of a portion of the plurality of sample images corresponding to a portion of the plurality of sample objects. The target object and the portion of the plurality of sample objects may be of a substantially same or similar age when the target image and the portion of the plurality of sample images are acquired, respectively. The target object and the portion of the plurality of sample objects may be of a same gender. Merely by way of example, the processing device 400a may determine a first ranking of the morphological characteristic value of the target region among the portion of the plurality of morphological characteristic values, and assess the condition of the organ or tissue of the target object based on the first ranking.

In some embodiments, the processing device 400a may determine a second ranking of the morphological characteristic values of the sample regions in the plurality of sample images based on age of the sample object in each of the plurality of sample images when each sample image is acquired. The processing device 400a may determine at least one grade of the morphological characteristic values corresponding to each age based on the second ranking corresponding to the each age. The processing device 400a may determine a third ranking of the morphological characteristic value of the target region in the target image among a portion of the morphological characteristic values of a portion of the plurality of sample images corresponding to a portion of the plurality of sample objects based on the at least one grade. The processing device 400a may assess the condition of the organ or tissue of the target object based on the third ranking. The target object and the portion of the plurality of sample objects may be of a substantially same or similar age when the target image and the portion of the plurality of sample images are acquired, respectively. Exemplary grades may include a percentile value.

In some embodiments, the processing device 400a may determine a relation of the morphological characteristic values corresponding to the plurality of sample objects and age of each of the plurality of sample objects when each of the plurality of sample images is acquired. For example, the processing device 400a may fit out a curve representing the relation of the morphological characteristic values corresponding to the plurality of sample objects and the age of each of the plurality of sample objects when the each of the plurality of sample images is acquired. The processing device 400a may determine a grade of the morphological characteristic value corresponding to the target object among a portion of the morphological characteristic values of a portion of the plurality of sample images that correspond to a portion of the plurality of sample objects based on age of the target object, the morphological characteristic value of the target object, and the relation. The target object and the portion of the plurality of sample objects may be of a substantially same or similar age when the target image and the portion of the plurality of sample images are acquired, respectively.

In some embodiments, the processing device 400a may obtain a second target image of the target object, a third target image of the target object, etc. (e.g., follow-up data of the target object as described in FIG. 7). The target image and the second target image (and the third target image, etc.) may be acquired at different ages. The processing device 400a may segment a second target region corresponding to the sub-region of the organ or tissue from the second target image, and determine a second morphological characteristic value of the second target region in the second target image. The processing device 400a may determine a target variation trend (see, e.g., FIGS. 12-14) of the morphological characteristic value corresponding to the target object based on the morphological characteristic value and the second morphological characteristic value corresponding to the target object. The processing device 400a may obtain a reference variation trend associated with the sample organ or tissue of at least a portion of the plurality of sample objects. The at least a portion of the plurality of sample objects may have a normal condition in the sample organ or tissue. The processing device 400a may assess the condition of the organ or tissue of the target object by comparing the target variation trend and the reference variation trend. More descriptions regarding the assessment of the condition of the organ or tissue of the target object may be found elsewhere in the present disclosure (e.g., FIGS. 5D-7 and the description thereof).

FIG. 5B is a flowchart illustrating an exemplary process for determining a target artificial intelligence model according to some embodiments of the present disclosure. In some embodiments, the process 500b may be performed by the processing device 400a online. In some embodiments, the process 500b may be performed by the processing device 400b offline. In some embodiments, the processing device 400b may be part of the image processing system 100. In some embodiments, the processing device 400b may be part of an external device (e.g., a processing device of a manufacturer of the scanner 110). Merely by way of example, the process 500b may be implemented as a set of instructions (e.g., an application) stored in a storage device of the external device. In some embodiments, the processing device 400b of the external device (e.g., one or more modules illustrated in FIG. 4B) may execute the set of instructions and may accordingly be directed to perform the process 500b. In the following descriptions, one or more operations of process 500b performed by the processing device 400b are merely provided for the purposes of illustration, and not intended to limit the scope of the present disclosure.

In 521, the processing device 400b (e.g., the acquisition module 422) may obtain a plurality of training images associated with a sample organ or tissue of at least one sample object.

The sample organ or tissue may correspond to the organ or tissue of the target object. For example, if the organ or tissue includes the brain of the target object, the sample organ or tissue may include the brain of the sample object(s). In some embodiments, the plurality of training images corresponding to the at least one sample object may be of one or more modalities, such as MR images, CT images, PET images, PET-CT images, PET-MR images, or the like. In some embodiments, the plurality of training images may include different types of images of a same modality. For example, for MR image, the different types may include T1-weighted images, T2-weighted images, T2*-weighted images, FLAIR images, or the like.

In some embodiments, the training images may be of a same modality as that of the target image. For example, if the target image is an MR image, the training images may be MR images. As another example, if the target image is a T1-weighted image, the training images may be of different types including T1-weighted images, T2-weighted images, T2*-weighted images, FLAIR images, or the like. In some embodiments, the training images may be of different modalities including at least a modality of the target image. For example, if the target image is an MR image, a portion of the training images may be MR images.

In some embodiments, the training images may be obtained from the scanner 110, the storage device 150, an external storage device that can communicate with the image processing system 100 (e.g., via the network 120)), a public database, a non-public database, etc. In some embodiments, the training images may include a sample organ or tissue of a plurality of sample objects. In some embodiments, the sample objects may be of various ages or age ranges. In some embodiments, the sample objects may be of one or more races. In some embodiments, the sample objects may have one or more disease labels. In some embodiments, different sample objects may have different disease labels. In some embodiments, the training images may be generated according to one or more scanning protocols. In some embodiments, different training images may be generated according to different scanning protocols. More descriptions of the training images may be found in Chinese Patent Application No. 201811126495.7 entitled "SYSTEMS, METHODS AND STORAGE MEDIUMS FOR AUTOMATIC MEDICAL IMAGE SEGMENTATION BASED ON MULTI ATLASES." filed Sep. 26, 2018, the contents of which are hereby incorporated by reference.

In 523, the processing device 400b (e.g., the training module 424) may obtain an initial artificial intelligence model.

The initial artificial intelligence model may include an initial deep learning model such as an initial CNN model (e.g., an initial 3D CNN model), an initial deep CNN (DCNN) model, an initial Fully Convolutional Network (FCN) model, an initial Recurrent Neural Network (RNN) model, an initial U-Net model, an initial V-Net model, etc. The initial artificial intelligence model may include one or more preliminary parameters that may be updated or optimized in a training process.

In 525, the processing device 400b (e.g., the training module 424) may determine the target artificial intelligence model by training the initial artificial intelligence model using the plurality of training images.

Taking an initial 3D CNN model as an example, each of the plurality of training images may be input to the initial 3D CNN model. The initial 3D CNN model may output a segmented image corresponding to each training image as a processing result. The processing device 400b may obtain or retrieve a pre-segmented image corresponding to each training image as a reference. The training process may be an iterative process. For example, the processing device 400b may compare the processing result with the reference, and determine whether a preset condition is satisfied. If the preset condition is satisfied, a trained 3D CNN model may be determined. If the preset condition is not satisfied, another training image may be input into the 3D CNN model, and one or more parameters (e.g., one or more weights) of the 3D CNN model may be updated based on the input, the processing result, and/or the reference. In some embodiments, the preset condition may relate to a difference between the processing result and the reference. For example, if the difference is less than or equal to a threshold, the iteration may terminate, and the target artificial intelligence model may be finalized.

In some embodiments, the trained 3D CNN model may be updated based on a plurality of updated or newly obtained training images periodically or non-periodically. The updating may be automatically triggered, or manually triggered by a user (e.g., an operator of the processing device 400b).

It should be noted that the above description of process 500b is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the training images may be divided into a training set (of training images) and a test set (of training images). In some embodiments, a reference anatomical atlas corresponding to each training image may be obtained. In some embodiments, the initial artificial intelligence model may be trained using the training images of the training set and reference anatomical atlases corresponding to the training images of the training set, and an intermediate artificial intelligence model may be obtained. In some embodiments, the training images of the test set may be input to the intermediate artificial intelligence model, and predicted anatomical atlases corresponding to the training images of the test set may be generated. In some embodiments, an overlap rate of one or more segmentation regions in the predicted anatomical atlases corresponding to the training images of the test set and one or more corresponding segmentation regions in the reference anatomical atlases corresponding to the training images of the test set may be determined. In some embodiments, a count of segmentation regions in each of which the overlap rate is larger than or equal to a first threshold may be determined. In some embodiments, the count may be compared with a second threshold. In some embodiments, if the count is larger than or equal to the second threshold, the intermediate artificial intelligence model may be designated as the target artificial intelligence model. More descriptions of the anatomical atlases and the training process of the artificial intelligence model may be found in Chinese Patent Application No. 201811126495.7 entitled "SYSTEMS, METHODS AND STORAGE MEDIUMS FOR AUTOMATIC MEDICAL IMAGE SEGMENTATION BASED ON MULTI ATLASES." filed Sep. 26, 2018, the contents of which are hereby incorporated by reference.

FIG. 5C is a flowchart illustrating an exemplary process for determining a relation between morphological characteristic values corresponding to a plurality of sample objects and age of each of the plurality of sample objects when each of a plurality of sample images is acquired according to some embodiments of the present disclosure. In some embodiments, the process 500c may be performed by the processing device 400a online. In some embodiments, the process 500c may be performed by the processing device 400b offline. In some embodiments, the process 500c may be performed by the processing device 400c offline. In some embodiments, the processing device 400c may be part of the imaging processing system 100. In some embodiments, the processing device 400c may be part of an external device (e.g., a processing device of a hospital or a medical institution). Merely by way of example, the process 500c may be implemented as a set of instructions (e.g., an application) stored in a storage device of the external device. In some embodiments, the processing device 400c of the external device (e.g., one or more modules illustrated in FIG. 4C) may execute the set of instructions and may accordingly be directed to perform the process 500c. In the following descriptions, one or more operations of process 500c performed by the processing device 400c are merely provided for the purposes of illustration, and not intended to limit the scope of the present disclosure.

In 531, the processing device 400c (e.g., the acquisition module 432) may obtain a plurality of sample images of the plurality of sample objects. The plurality of sample images may be the same as or similar to the plurality of training images as described in FIG. 5B, and will not be described here. In some embodiments, the sample objects described in FIG. 5C and sample objects described in 547 of FIG. 5A may be the same. In some embodiments, the sample objects described in FIG. 5C and sample objects described in FIG. 5B may be the same, partially overlapping (at least one sample object described in FIG. 5C also being a sample object described in FIG. 5B), or totally different (no sample object described in FIG. 5C being a sample object described in FIG. 5B).

In 533, the processing device 400c (e.g., the acquisition module 432) may obtain age of each of the plurality of sample objects when each of the plurality of sample images is acquired. The age of each of the plurality of sample objects may be presented by an integer, such as 50 years old, 61 years old, or be accurate to one decimal place such as 60.1 years old, 60.5 years old. In some embodiments, information (e.g., name, age, gender, etc.) of each sample object may be registered and stored in a storage device when or before each sample image of each sample object is acquired. The processing device 400c may retrieve the age directly from the storage device (e.g., via the network 120). In some embodiments, the ages of the plurality of sample objects may include the age of the target object. Alternatively, at least a portion of the sample objects and the target object may be of a substantially same or similar age when the target image and the sample images of the portion of the sample objects are acquired, respectively.

In 535, the processing device 400c (e.g., the segmentation module 434) may segment a sample region from each of the plurality of sample images. The processing device 400c may segment the sample region in each of the plurality of sample images similarly to how the processing device 400a segment the target region from the target image as described with respect to 513, and relevant descriptions of which are not repeated here.

In 537, the processing device 400c (e.g., the determination module 436) may determine a morphological characteristic value of the sample region in each sample image. The determination of the morphological characteristic value of the sample region in each sample image may be similar to the determination of the morphological characteristic value of the target region in the target image as described with respect to 545 in FIG. 5A, and relevant descriptions of which are not repeated here.

In 539, the processing device 400c (e.g., the determination module 436) may determine the relation between the morphological characteristic values corresponding to the plurality of sample objects and the age of each of the plurality of sample objects when each of the plurality of sample images is acquired.

In some embodiments, the processing device 400c may determine the first relation as described with respect to 547 in FIG. 5A based on morphological characteristic values corresponding to a first portion of the plurality of sample objects and age of each of the first portion of the plurality of sample objects. The processing device 400c may determine the second relation as described with respect to 547 in FIG. 5A based on morphological characteristic values corresponding to a second portion of the plurality of sample objects and age of each of the second portion of the plurality of sample objects. Each sample object of the first portion of the plurality of sample objects may have a normal condition in the corresponding sample region. Each sample object of the second portion of the plurality of sample objects may have an abnormal condition in the corresponding sample region.

In some embodiments, the processing device 400c may determine the relation(s) by fitting out a curve representing the relation, based on the morphological characteristic values corresponding to the plurality of sample objects and the age of each of the plurality of sample objects when each of the plurality of sample images is acquired. More descriptions regarding the determination of the fitted curve may be similar to and/or found elsewhere in the present disclosure (e.g., FIG. 6 and the description thereof).

It should be noted that the above descriptions regarding the processes 500a-500c are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, each process of the processes 500a-500c may be accomplished with one or more additional operations not described and/or without one or more of the operations discussed above. Additionally, the order of the processes 500a-500c may not be intended to be limiting. In some embodiments, the processes 500a-500c may be accomplished by another processing device, such as the processing device 400d.

FIG. 5D is a flowchart illustrating an exemplary medical image processing process according to some embodiments of the present disclosure. In some embodiments, the process 500d may be performed by the processing device 400d.

In 501, a plurality of sample images and age of a sample object in each sample image of the plurality of sample images may be acquired. In some embodiments, operation 501 may be performed by the sample data acquisition module 402.

In some embodiments, a plurality of images of normal people may be collected as the sample images, and age of each normal people of the plurality of normal people may be acquired. The normal people may refer to people of which a sample organ or tissue of interest (e.g., the brain) is in a normal condition when a corresponding sample image is collected. In some embodiments, the normal people may be selected as sample objects. A sample organ or tissue may refer to an organ or tissue of a sample object. For example, at least one hospital may select volunteers as sample objects and obtain images of a specific organ or tissue and/or ages of the volunteers. In some embodiments, one or more images of the specific organ or tissue of one or more sample objects within a certain age group may be acquired as the sample images. For example, images of the specific organ or tissue of sample objects within an age group ranging from 20 to 90 years old may be acquired as the sample images. In some embodiments, gender of the sample object in each sample image may be acquired. In some embodiments, images of the specific organ or tissue of sample objects of a specific gender may be acquired as the sample images. Taking brain images as an example, in some embodiments, a plurality of MR brain images may be acquired as brain sample images. For example, one or more T1-weighted images, one or more T2-weighted images, one or more FLAIR images, or the like, or a combination thereof of the brain may be acquired.

In 503, a first sample region corresponding to a first sub-region of a sample organ or tissue may be segmented from each sample image. In some embodiments, operation 503 may be performed by the image segmentation module 406.

In some embodiments, the sample images may be segmented using at least one image segmentation algorithm. In some embodiments, the sample images may be segmented using a deep learning model. In some embodiments, the deep learning model may be a 3D CNN. The 3D CNN may be used to process images of an entire organ or tissue. In some embodiments, the sample images may be segmented using a template matching algorithm. The template matching algorithm may include a single template matching algorithm, a multi-template matching algorithm, etc.

Taking the brain sample images as an example, in some embodiments, each brain sample image may be segmented into at least one brain sample region corresponding to a sub-region of the brain. Exemplary brain sub-regions may include the whole brain, the grey matter, the white matter, the amygdala, the putamen, the hippocampus, the globus pallidus, the thalamus, the anterior cingulate cortex, the middle cingulate cortex, the posterior cingulate cortex, the insula, the superior temporal gyrus, the middle temporal gyrus, the temporal pole, etc.

In 505, a morphological characteristic value of the first sample region in each sample image may be determined. In some embodiments, operation 505 may be performed by the morphological characteristic determination module 408.

In some embodiments, at least one morphological characteristic value of the first sample region may be determined. In some embodiments, the morphological characteristic value(s) of the first sample region may be determined using at least one morphometry technique. Exemplary morphometry techniques may include a voxel-based morphometry technique, a tensor-based morphometry technique, a deformation-based morphometry technique, or the like. Taking the brain images as an example, morphological characteristics of the brain images may include but not limited to a volume, a cortical thickness, a cortex area, a gyrification index, or the like.

In 507, a target image of a target object and age of the target object may be acquired. In some embodiments, operation 507 may be performed by the target data acquisition module 404.

In some embodiments, if the plurality of sample images are of a same modality, the target image may be of the same modality as the plurality of sample images. In some embodiments, if the plurality of sample images are of different modalities, the target image may be of a modality that is the same as that of at least a portion of the sample images. In some embodiments, an accuracy of the age of the target object may be consistent with an accuracy of the ages of the sample objects in the sample images. For example, the age of the target object and the ages of the sample objects may both be integers or being accurate to one decimal place. In some embodiments, follow-up data of the target object may be obtained. The follow-up data may include a plurality of target images of the target object. The target images may be collected at different ages of the target object.

In 509, a first target region corresponding to a first sub-region of an organ or tissue may be segmented from the target image. The sample organ or tissue may be of a same type as the organ or tissue of the target object. In some embodiments, operation 509 may be performed by the image segmentation module 406.

In some embodiments, the first target region segmented by the image segmentation module 406 from the target image may be of the same type as the first sample region segmented by the image segmentation module 406 from the sample image(s). For example, taking the brain images as an example, the image segmentation module 406 may segment, from both the target image and the sample image(s), the whole brain, the grey matter, the white matter, the amygdala, the putamen, the hippocampus, the globus pallidus, the thalamus, the anterior cingulate cortex, the middle cingulate cortex, the posterior cingulate cortex, the insula, the superior temporal gyrus, the middle temporal gyrus, the temporal pole, etc. The first target region may be segmented in 509 similarly to how the first sample region is segmented as described with respect to 503, and relevant descriptions of which are not repeated here.

In 511, a morphological characteristic value of the first target region in the target image may be determined. In some embodiments, operation 511 may be performed by the morphological characteristic determination module 408.

In some embodiments, the morphological characteristic of the first target region determined by the morphological characteristic determination module 408 may be of the same type as the morphological characteristic of the first sample region determined by the morphological characteristic determination module 408. The morphological characteristic value of the first target region may be determined in 511 similarly to how the morphological characteristic value of the first sample region is determined as described with respect to 505, and relevant descriptions of which are not repeated here.

In 513, a condition of the organ or tissue of the target object may be determined based on age of each of one or more sample objects in at least one portion of the plurality of sample images, a morphological characteristic value of a first sample region in each one of the at least one portion of the plurality of sample images, the age of the target object, and the morphological characteristic value of the first target region. In some embodiments, operation 513 may be performed by the analysis module 410.

In some embodiments, a ranking of the morphological characteristic value of the first target region among morphological characteristic values of first sample regions of a portion of the plurality of sample images may be determined, and a condition of the brain atrophy of the target object may be determined according to the ranking. Sample objects in the portion of the plurality of sample images and the target object may be of a same age (or a substantially same or similar age) when the target image and the portion of the plurality of sample images are acquired, respectively. In some embodiments, the same age may refer to a substantially same or similar age, specifically may refer to any age within a certain age range. For example, 60 years old may be substantially the same as or similar to any age between 59.5 years old and 60.5 years old. In some embodiments, a grade of the morphological characteristic value of the first target region in the ranking may be determined. For example, the portion of sample images may be determined from the plurality of sample images, such that sample objects in the portion of sample images are of a same age as the target object. The morphological characteristic values of the first target region in the target image and the first sample regions in the portion of the plurality of sample images may be ranked according to a ranking rule (e.g., in a descending order or ascending order). Thereby, the grade of the morphological characteristic value of the first target region in the ranking may be determined. In some embodiments, a grade range of the morphological characteristic value of the first target region in the ranking may be determined. In some embodiments, the grade range may refer to a percentile value of the morphological characteristic value of the first target region in the ranking. For example, the grade range (or the percentile value) may be determined by dividing the grade in the ranking by a total number (or count) of the portion of the plurality of sample images.

In some embodiments, the morphological characteristic value of a region of an image (corresponding to a sub-region of an organ or tissue) may relate to a condition of the organ or tissue.

In some embodiments, if the morphological characteristic value associated with a sub-region of an organ or tissue is relatively small, the condition of the organ or tissue of an object (e.g., a person) may be relatively bad. Alternatively, if the morphological characteristic value associated with a sub-region of an organ or tissue is relatively large, the condition of the organ or tissue of an object (e.g., a person) may be relatively bad. Taking the brain as an example, for a first type of brain sub-regions, if the morphological characteristic value associated with a brain sub-region of the first type is relatively small, the brain atrophy may be relatively severe. Exemplary first type of brain sub-regions may include the whole brain, the whole brain cortex, the gyrus, the hippocampus, the gray matter, the white matter, the putamen, the temporal lobe, the entorhinal cortex, the corpus callosum, the temporoparietal cortex, etc. If a target region of a target image corresponds to a first type of brain sub-region of a target object, and the target object has a risk of brain atrophy, the morphological characteristic value of the target region may be smaller than the morphological characteristic values of sample regions (corresponding to a same type of brain sub-region as the target object) in one or more of the plurality of sample images. The sample objects in the one or more sample images and the target object may be of a substantially same or similar age when the target image and the one or more sample images are acquired, respectively. If the number (or count) of the sample objects in the one or more sample images is relatively large (i.e., the morphological characteristic value associated with the target object is smaller than that associated with a large number of sample objects), the risk of the brain atrophy of the target object may be relatively high. If the morphological characteristic values of the target region and the sample regions are ranked in a descending order, and the morphological characteristic value of the target region is ranked at a relatively low grade (e.g., bottom N), then the risk of the brain atrophy of the target object may be relatively high. Alternatively, if the morphological characteristic values of the target region and the sample regions are ranked in an ascending order, and the morphological characteristic value of the target region is ranked at a relatively high grade (e.g., top N), then the risk of the brain atrophy of the target object may be relatively high. For a second type of brain sub-regions, if the morphological characteristic value associated with a brain sub-region of the second type is relatively large, the brain atrophy may be relatively severe. Exemplary second type of brain sub-regions may include the ventricle, the choroid fissure, the sulcus, the cingulate sulcus, the parietooccipital sulcus, etc. If a target region of a target image corresponds to a second type of brain sub-region of a target object, and the target object has a risk of brain atrophy, the morphological characteristic value of the target region may be larger than the morphological characteristic values of sample regions (corresponding to a same type of brain sub-region as the target object) in one or more of the plurality of sample images. The sample objects in the one or more sample images and the target object may be of a substantially same or similar age when the target image and the one or more sample images are acquired, respectively. If the number (or count) of the sample objects in the one or more sample images is relatively large (i.e., the morphological characteristic value associated with the target object is larger than that associated with a large number of sample objects), the risk of the brain atrophy of the target object may be relatively high. Similarly, the risk of the brain atrophy of the target object may be determined based on a ranking rule and/or the grade of the target object.

In some embodiments, one or more curves representing a trend of a morphological characteristic value associated with a sub-region of a sample organ or tissue of normal people varying with age may be fitted out based on the plurality of sample images and the age of each sample object in each of the plurality of sample images. In some embodiments, a percentile value of the morphological characteristic value associated with the target object in the ranking of the morphological characteristic values associated with sample objects (that are of a substantially same or similar age as the target object) may be determined based on the fitted curve (s). More descriptions regarding the determination of the percentile value in the ranking based on the fitted curve(s) may be found elsewhere in the present disclosure (e.g., FIG. 6 and descriptions thereof).

In some embodiments, a ranking of the morphological characteristic value associated with a specific sub-region of the target object among the morphological characteristic values associated with the specific sub-region of sample objects (that are of a substantially same or similar age and/or a same gender as the target object) may be determined, and a condition of an organ or tissue of the target object may be determined according to the ranking.

In some embodiments, a trend of the morphological characteristic values associated with a specific sub-region of the target object varying with age (also referred to as a target variation trend of the morphological characteristic values of the target regions corresponding to the target object) may be determined according to follow-up data of the target object. In some embodiments, a trend of the morphological characteristic values associated with the specific sub-region of sample objects (e.g., normal people) varying with age (also referred to as a reference variation trend of the morphological characteristic values of sample regions corresponding to the sample objects) may be determined based on the sample images and the age of each sample object in each sample image. In some embodiments, the condition of the organ or tissue of the target object may be determined by comparing the target variation trend with the reference variation trend. More descriptions regarding the determination the condition of the organ or tissue of the target object by comparing the target variation trend with the reference variation trend may be found elsewhere in the present disclosure (e.g., FIGS. 7 and 12-14 and descriptions thereof).

It should be noted that the above description of the process 500*d* is merely provided for purposes of illustration, and not intended to limit the scope of the present disclosure. It should be understood that, after understanding the principle of the operations, persons having ordinary skills in the art may arbitrarily combine any operations, add or delete any operations, or apply the principle of the operations to other image processing process, without departing from the principle. For example, in some embodiments, a morphological characteristic value of a second target region corresponding to a second sub-region of the organ or tissue of the target object may be determined, and a ranking of the morphological characteristic value of the second target region among the morphological characteristics values of second sample regions corresponding to second sub-regions of the organ or tissue of the sample objects (that are of a substantially same or similar age as the target object) may be determined. In some embodiments, the condition of the organ or tissue of the target object may be comprehensively assessed based on the rankings corresponding to two or more sub-regions of the organ or tissue. In some embodiments, a sub-region associated with a relatively abnormal grade in the ranking(s) may be analyzed in the comprehensive assessment.

In some embodiments, the processing device 400*d* may be implemented by an image processing apparatus. The apparatus may include at least one processor and at least one storage device. The at least one storage device may be configured to store instructions. The at least one processor may be configured to execute at least a portion of the instructions to implement the image processing process as described in FIG. 5D.

In some embodiments, the processing device 400*d* may be implemented according to a computer readable storage medium. The storage medium may store instructions. When executed by at least one processor, the instructions may implement the image processing process as described in FIG. 5D.

FIG. 6 is a flowchart illustrating an exemplary process for determining a ranking of a morphological characteristic value associated with a sub-region (e.g., the first sub-region) of an organ or tissue of a target object among morphological characteristic values associated with the sub-region of the organ or tissue of sample objects that are of the same age as the target object according to some embodiments of the present disclosure.

In 601, at least one percentile value of morphological characteristic values of first sample regions in sample images corresponding to each age may be determined. The at least one percentile value corresponding to each age may be determined by determining a ranking of the morphological characteristic values of the first sample regions in the sample images corresponding to each age, based on age of the sample object in each sample image, and the morphological characteristic value of the first sample region in each sample image. In some embodiments, for sample images corresponding to a same age, the morphological characteristic values of the first sample regions in the sample images corresponding to the same age may be ranked in a descending order to determine a percentile. A specific value of the morphological characteristic value corresponding to a percentile may be designed as the percentile value of the percentile. For example, taking brain sample images as an example, Total Intracranial Volumes (TIVs) of the brain sample images corresponding to 60 years old people may be ranked in a descending order. If a TIV of a certain sample image is larger than the TIVs of 95% of the brain sample images, the TIV of the certain sample image may be the 95th percentile value among the TIVs corresponding to the 60 years old people. In some embodiments, for each age, a plurality of percentile values (e.g., the 5th percentile value, the 25th percentile value, the 50th percentile value, the 75th percentile value, the 95th percentile value, etc.) of the morphological characteristic values of the first sample regions may be determined. In some embodiments, the same age may refer to a substantially same or similar age, specifically may refer to any age within a certain age range. For example, 60 years old may be substantially the same as or similar to any age between 59.5 years old and 60.5 years old.

In 603, a curve representing a relation of the morphological characteristic values of the first sample regions in a plurality of sample images and ages of the sample objects in the plurality of sample images be fitted out by using age as an independent variable, and using the at least one percentile value of morphological characteristic values of first sample regions in sample images corresponding to each age as a dependent variable. In some embodiments, the curve fitting operation may be performed by using at least one regression analysis algorithm, including but not limited to a Locally Weighted Regression (Loess), a Polynomial Regression, a Ridge Regression, a Lasso Regression, etc. For illustration, a process of the curve fitting using the Loess as an example may be described as follows.

According to the Loess, Equation (1) is an error function, and a parameter θ may be obtained by minimizing the value of the error function through fitting the parameter θ:

$$J(\theta)=\Sigma_{i=1}^{m} w^{(i)}[y^{(i)}-\theta^T x^{(i)}]^2, \quad (1)$$

where J(θ) is a total error of predicted values and true values of percentile values of morphological characteristic values of first sample regions corresponding to all ages (associated with the plurality of sample images); m is the total number (or count) of the ages; $w^{(i)}$ is a weight of an i-th age, reflecting a contribution of the age to the total error; $y^{(i)}$ is a true value of a percentile value of a morphological characteristic value of the first sample region corresponding to the i-th age; $x^{(i)}$ is the i-th age; $\theta^T x^{(i)}$ is a predicted value of the percentile value of the morphological characteristic value of the first sample region corresponding to the i-th age. The fitted curve may be presented using $x^{(i)}$ as the abscissa, and $\theta^T x^{(i)}$ as the ordinate.

The weight $w^{(i)}$ may be determined as follows:

$$w^{(i)} = e^{-\frac{(x^{(i)}-x)^2}{2k^2}}, \quad (2)$$

where x is an independent variable used to predict a percentile value of a morphological characteristic value of a first sample region corresponding to the age of x; $x^{(i)}$ is the i-th age; k is a bandwidth parameter, controlling a width of $w^{(i)}$ (a bell-shaped function). It may be understood that if an age is relatively close to the independent variable x, then the contribution of the age to the total error may be relatively great. Alternatively, if the difference between an age and the independent variable x is relatively large, then the contribution of the age to the total error may be relatively small. In some embodiments, k may be determined according to experiences.

FIG. 11 is a schematic diagram illustrating exemplary curves representing a relation of percentile values of TIVs of normal females and ages of the normal females according to some embodiments of the present disclosure. The curves may be fitted based on sample images. As shown, the independent variable (i.e., the abscissa) may be age, and the dependent variable (i.e., the ordinate) may be TIV. 1102 may indicate a curve representing a relation of 95th percentile values of TIVs of normal females and ages of the normal females. A 95th percentile value corresponding to an age may indicate that TIVs of 95% of the sample images corresponding to the age are smaller than a TIV corresponding to the 95th percentile value. 1104 may indicate a curve representing a relation of 75th percentile values of TIVs of normal females and ages of the normal females. A 75th percentile value corresponding to an age may indicate that TIVs of 75% of the sample images corresponding to the age are smaller than a TIV corresponding to the 75th percentile value. 1106 may indicate a curve representing a relation of 50th percentile values of TIVs of normal females and ages of the normal females. A 50th percentile value corresponding to an age may indicate that TIVs of 50% of the sample images corresponding to the age are smaller than a TIV corresponding to the 50th percentile value. 1108 may indicate a curve representing a relation of 25th percentile values of TIVs of normal females and ages of the normal females. A 25th percentile value corresponding to an age may indicate that TIVs of 25% of the sample images corresponding to the age are smaller than a TIV corresponding to the 25th percentile value. 1110 may indicate a curve representing a relation of 5th percentile values of TIVs of normal females and ages of the normal females. A 5th percentile value corresponding to an age may indicate that TIVs of 5% of the sample images corresponding to the age are smaller than a TIV corresponding to the 5th percentile value. As shown in FIG. 11, certain percentile values of TIVs of normal females may generally decrease with age.

In 605, a percentile value of the morphological characteristic value of a first target region in a target image among the morphological characteristic values of the first sample regions in a portion of the plurality of sample images may be determined by comparing age of the target object and the morphological characteristic value of the first target region in the target image with the fitted curve. The sample objects in the portion of the plurality of sample images and the target object may be of a substantially same or similar age when the target image and the portion of the plurality of sample images are acquired, respectively.

In some embodiments, a percentile value range of the first target region in the target image among the morphological characteristic values of the first sample regions in the portion of the plurality of sample images may be determined. For example, the age of the target object, the morphological characteristic value of the first target region of the target object, and the fitted curve may be put in a same coordinate system, and the percentile value (range) of the first target region in the target image among the morphological characteristic values of the first sample regions in the portion of the plurality of sample images may be determined intuitively (or instantly). Merely by way of example, if the target object is a female of 60 years old and the TIV of the target object is 1400000 mm$^3$, the percentile value range of the TIV of the target object may be from 5% to 25% according to FIG. 11. In some embodiments, a specific percentile value of the morphological characteristic value of the first target region among the morphological characteristic values of the first sample regions in the portion of the plurality of sample images may be determined. Specifically, in some embodiments, the morphological characteristic value of the first target region and the morphological characteristic values of the first sample regions in the portion of the plurality of sample images may be ranked, and the specific percentile value of the morphological characteristic value of the first target region among the morphological characteristic values of the first sample regions in the portion of the plurality of sample image may be determined based on the ranking. Additionally, or alternatively, in some embodiments, a second curve corresponding to females of 60 years old may be fitted out by using TIV as a dependent variable and using the percentile values (e.g., the five percentile values corresponding to females of 60 years old illustrated in FIG. 11) as an independent variable. In some embodiments, a specific percentile value corresponding to the target object of 60 years old may be determined based on the second fitted curve and the TIV of the target object.

In 607, a condition of an organ or tissue of the target object may be determined based on the percentile value.

In some embodiments, if the morphological characteristic value associated with a sub-region of an organ or tissue is relatively small, the condition of the organ or tissue of an object (e.g., a person) may be relatively bad. Alternatively, if the morphological characteristic value associated with a sub-region of an organ or tissue is relatively large, the condition of the organ or tissue of an object (e.g., a person) may be relatively bad. Taking the brain as an example, for a first type of brain sub-regions, if the morphological characteristic value associated with a brain sub-region of the first type is relatively small, the brain atrophy may be relatively severe. For example, if the TIV is relatively small, the brain atrophy may be relatively severe. If a target region of a target image corresponds to a first type of brain sub-region of a target object, and the morphological characteristic value of the target region is smaller than the morphological characteristic values associated with a certain proportion of sample objects that are of a substantially same or similar age as the target object, then the risk of the brain atrophy of the target object may be relatively high. For example, if a target region of a target image corresponds to a first type of brain sub-region of a target object, and the percentile value of the morphological characteristic value associated with the target object among the morphological characteristic values associated with sample objects (that are of a substantially same or similar age as the target object) is equal to or less than 5%, that is, morphological characteristic values associated with no larger than 5% of the sample objects (that are of a substantially same or similar age as the target object) are less than the morphological characteristic value associated with the target object, then the risk of the brain atrophy of the target object may be considered to be relatively high. If the percentile value of the morphological characteristic value associated with the target object among the morphological characteristic values associated with sample objects (that are of a substantially same or similar age as the target object) is greater than 5% and equal to or less than 25% (i.e., morphological characteristic values associated with 5%-25% of the sample objects (that are of a substantially same or similar age as the target object) are less than the morphological characteristic value associated with the target object), the risk of the brain atrophy of the target object may be considered to be medium. If the percentile value of the morphological characteristic value associated with the target object among the morphological characteristic values associated with sample objects (that are of a substantially same or similar age as the target object) is greater than 25% (i.e., morphological characteristic values associated with >25% of the sample objects (that are of a substantially same or similar age as the target object) are less than the morphological characteristic value associated with the target object), then the risk of the brain atrophy of the target object may be considered to be relatively low.

For a second type of brain sub-regions, if the morphological characteristic value of a brain sub-region is relatively large, the brain atrophy may be relatively severe. For example, if the volume of the ventricle is relatively large, the brain atrophy may be relatively severe. If a target region of a target image corresponds to a second type of brain sub-region of a target object, and the morphological characteristic value of the target region is larger than the morphological characteristic values associated with a certain proportion of sample objects that are of a substantially same or similar age as the target object, then the risk of the brain atrophy of the target object may be relatively high. For example, if a target region of a target image corresponds to a second type of brain sub-region, and the percentile value of the morphological characteristic value associated with the target object among the morphological characteristic values associated with sample objects (that are of a substantially same or similar age as the target object) is equal to or larger than 95%, that is, morphological characteristic values associated with no larger than 5% of the sample images (that are of a substantially same or similar age as the target object) are greater than the morphological characteristic value associated with the target object, then the risk of the brain atrophy of the target object may be considered to be relatively high. If the percentile value of the morphological characteristic value associated with the target object among the morphological characteristic values associated with sample objects (that are of a substantially same or similar age as the target object) is less than 95% and equal to or greater than 75% (i.e., morphological characteristic values associated with 75%-95% of the sample objects (that are of a substantially same or similar age as the target object) are less than the morphological characteristic value associated with the target object), the risk of the brain atrophy of the target object may be considered to be medium. If the percentile value of the morphological characteristic value associated with the target object among the morphological characteristic values associated with sample objects (that are of a substantially same or similar age as the target object) is less than 75% (i.e., morphological characteristic values associated with <75% of the sample objects (that are of a substantially same or similar age as the target object) are less than the morphological characteristic value associated with the target object), the risk of the brain atrophy may be considered to be relatively low.

Figure 7:
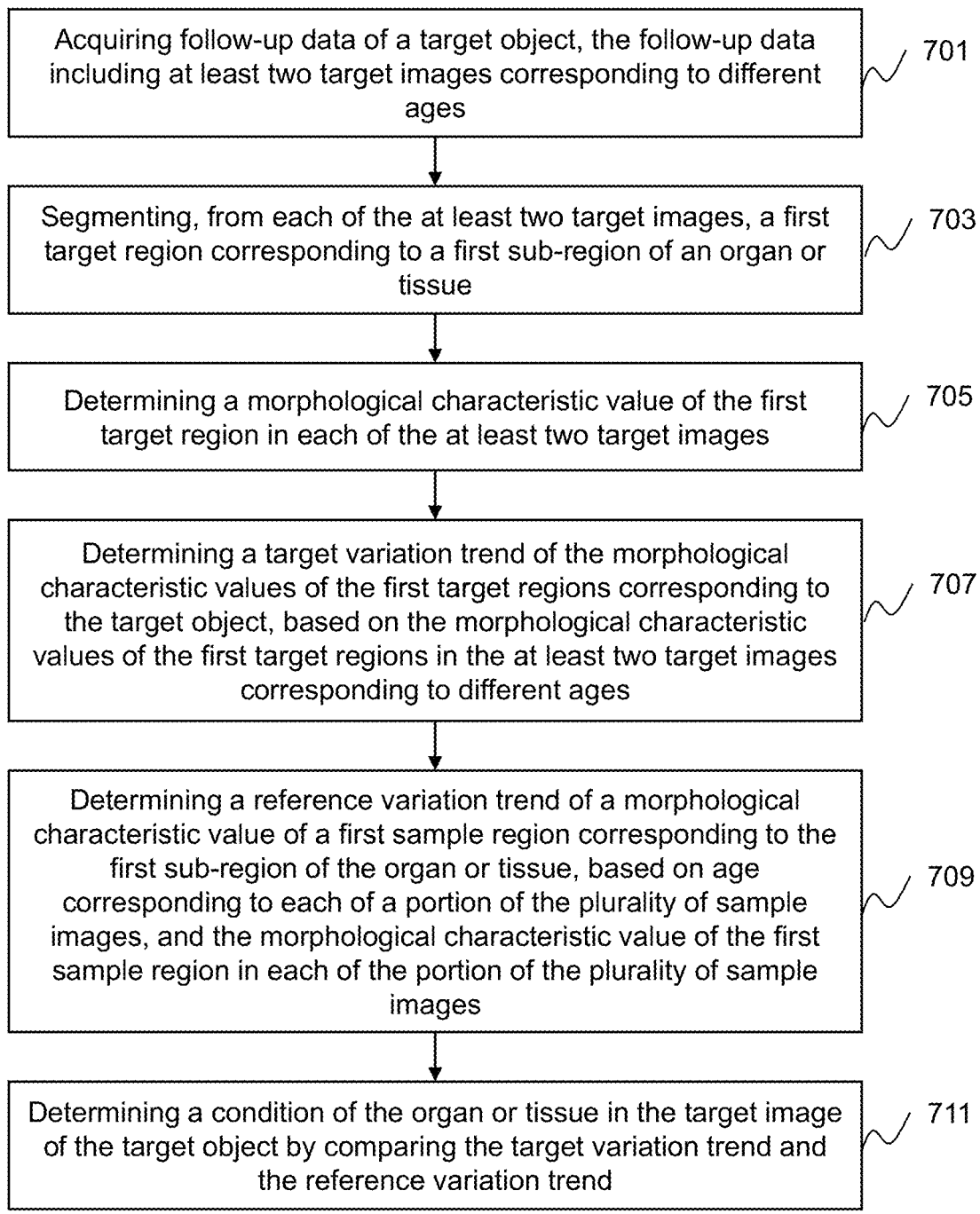
FIG. 7 is a flowchart illustrating an exemplary process for determining a condition of an organ or tissue of a target object based on a target variation trend of morphological characteristic values associated with the target object according to some embodiments of the present disclosure.

FIG. 7 is a flowchart illustrating an exemplary process for determining a condition of an organ or tissue of a target object based on a target variation trend of morphological characteristic values associated with the target object according to some embodiments of the present disclosure.

In 701, follow-up data of the target object may be acquired. The follow-up data may include at least two target images corresponding to different ages. The age(s) may be presented by an integer, or may be accurate to at least one decimal place. In some embodiments, a target image may be collected at a regular time interval (e.g., every six months, every year, every year and a half, every two years, etc.).

In 703, a first target region corresponding to a first sub-region of the organ or tissue may be segmented from each of the at least two target images. The first target region may be segmented in 703 similarly to how the first sample region is segmented as described with respect to 503 in FIG. 5, and relevant descriptions of which are not repeated here.

In 705, a morphological characteristic value of the first target region in each of the at least two target images may be determined. The morphological characteristic value of the first target region may be determined in 705 similarly to how the morphological characteristic value of the first sample region is determined as described with respect to 505 in FIG. 5, and relevant descriptions of which are not repeated here.

In 707, a target variation trend of the morphological characteristic values of the first target regions corresponding to the target object may be determined based on the morphological characteristic values of the first target regions in the at least two target images corresponding to different ages.

In some embodiments, the target variation trend of the morphological characteristic values of the first target regions corresponding to the target object may be determined qualitatively. For example, according to the target variation trend, the morphological characteristic values may decrease with age or increase with age. In some embodiments, the target variation trend of the morphological characteristic values of the first target regions corresponding to the target object may be determined quantitatively. For example, a variation rate of the morphological characteristic values of the first target regions corresponding to the target object (also referred to as a target variation rate) may be determined. Specifically, a curve may be plotted using age of the target object as the abscissa, and the morphological characteristic value of the first target region as the ordinate. A slope of the curve may be determined as the target variation rate. As another example, a line (e.g., a straight line) representing a variation of the morphological characteristic value of the first target region corresponding to the target object with age (within an age range corresponding to the follow-up data of the target object) may be fitted out.

In 709, a reference variation trend of a morphological characteristic value of a first sample region corresponding to the first sub-region of the organ or tissue may be determined based on age corresponding to each of a portion of the plurality of sample images, and the morphological characteristic value of the first sample region in each of the portion of the plurality of sample images.

In some embodiments, the reference variation trend of the morphological characteristic value of the first sample region corresponding to the first sub-region of the organ or tissue may be determined qualitatively. In some embodiments, the reference variation trend of the morphological characteristic value of the first sample region corresponding to the first sub-region of the organ or tissue may be determined quantitatively. In some embodiments, a variation rate of the morphological characteristic value of the first sample region corresponding to the first sub-region of the organ or tissue with respect to age may be determined. In some embodiments, a variation rate of a percentile value of the morphological characteristic value of the first sample region corresponding to the first sub-region of the organ or tissue (also referred to as a reference variation rate) may be determined. For example, the curves in FIGS. 12-14 may represent exemplary reference variation trends of percentile values of the gray matter volume, the white matter volume, and the putamen volume with respect to age, respectively. Slopes of the curves may represent reference variation rates of the corresponding percentile values of the grey matter volume, the white matter volume, and the putamen volume with respect to age, respectively. In some embodiments, according to a portion of brain sample images, a line (e.g., a straight line) representing the variation of a morphological characteristic value of a first sample region corresponding to the first sub-region of the brain with respect to age (within the age range corresponding to the follow-up data of the target object) may be fitted out.

In some embodiments, if the sample objects include normal people, the reference variation trend of the morphological characteristic values may represent a normal variation trend associated with normal people.

In 711, the condition of the organ or tissue in the target image of the target object may be determined by comparing the target variation trend and the reference variation trend.

In some embodiments, the target variation trend and the reference variation trend may be compared qualitatively to determine the condition of the organ or tissue in the target image of the target object. For example, for normal people, morphological characteristic values associated with some sub-regions of the organ or tissue may not change significantly with age. If the morphological characteristic value associated with a sub-region of the target object changes significantly with age, then the condition of the organ or tissue of the target object may be considered to be at risk. More descriptions regarding the qualitative determination of the condition of the organ or tissue may be found elsewhere in the present disclosure (e.g., FIGS. 13-15 and the descriptions thereof).

In some embodiments, the target variation trend and the reference variation trend may be compared quantitatively to determine the condition of the organ or tissue in the target image of the target object. For example, the target variation rate and the reference variation rate may be compared. The condition of the organ or tissue of the target object may be determined based on a difference between the target variation rate and the reference variation rate. In some embodiments, at least one threshold may be set for the difference between the target variation rate and the reference variation trend. In some embodiments, a threshold for the difference between the target variation rate and the reference variation trend may relate to a risk grade of the organ or tissue of the target object. In some embodiments, the at least one threshold may be set according to a default setting of the image processing system 100 or preset by a user or operator via the terminals 130. In some embodiments, the at least one threshold may be set based on an empirical value, clinical statistics, or the like. In some embodiments, the thresholds may include a first threshold and a second threshold. The first threshold may be greater than the second threshold. If the target variation rate is greater than the reference variation rate, and the difference is greater than the first threshold, the organ or tissue of the target object may be considered to have a relatively high risk. If the target variation rate is greater than the reference variation rate, and the difference is greater than the second threshold but less than the first threshold, the organ or tissue of the target object may be considered to have a medium risk. If the target variation rate is greater than the reference variation rate, and the difference is less than the second threshold, the organ or tissue of the target object may be considered to have a relatively low risk. It should be noted that, in response to a determination that the difference is equal to the first threshold, the processing device 140 may determine that the organ or tissue of the target object has either a relatively high risk or a medium risk. In response to a determination that the difference is equal to the second threshold, the processing device 140 may determine that the organ or tissue of the target object has either a relatively low risk or a medium risk.

In some embodiments, an angle between the fitted line representing the variation of the morphological characteristic value associated with the target object with respect to age (also referred to as a target line) and a fitted line of a morphological characteristic value associated with sample objects with respect to age (also referred to as a reference line) may be determined, and the condition of the organ or tissue of the target object may be determined based on the angle. For example, the target line may be fitted out by using age as an independent variable and using the TIVs associated with the target object corresponding to different ages as a dependent variable. As another example, the reference line may be fitted out by using age as an independent variable and using average TIVs associated with the sample objects corresponding to different ages as a dependent variable.

Figure 13:
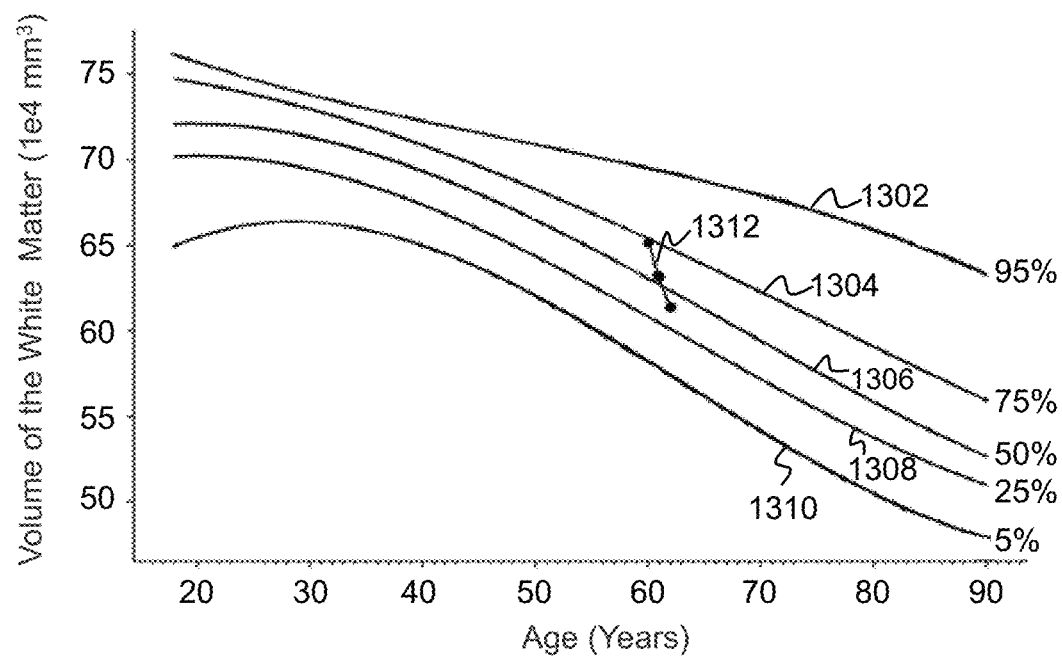
FIG. 13 is a schematic diagram illustrating an exemplary target variation trend of the white matter volume of the brain of a target object and exemplary reference variation trends according to some embodiments of the present disclosure.

In some embodiments, a reference line corresponding to certain percentile value may be fitted out by using age as an independent variable and using morphological characteristic values associated with the sample objects corresponding to different ages and the certain percentile value as a dependent variable. The target line may be compared with the reference line corresponding to the certain percentile value. For example, as shown in FIG. 13, the follow-up data of the target object may be collected at the age of 60 years old, 61 years old, and 62 years old. The target line 1312 may be fitted out using age as an independent variable and using the volumes of the white matter associated with the target object corresponding to ages of 60 years old, 61 years old, and 62 years old as a dependent variable. As the collection of the follow-up data begins at 60 years old and the percentile value associated with the target object (i.e., the percentile value of the volume of the white matter associated with the target object) at 60 years old is substantially 75%, a reference line corresponding to 75% may be fitted out using age as the independent variable and using the volumes of the white matter associated with the sample objects corresponding to ages of 60 years old, 61 years old, and 62 years old and the 75th percentile value as a dependent variable. The target line 1312 may be compared with the reference line corresponding to 75% to determine the condition of the brain in the target image of the target object.

In some embodiments, the reference variation trend may go down, and the target variation trend may also go down. In some embodiments, the target variation trend may deteriorate with respect to the reference variation trend (e.g., the target line may be below the reference line). It may be understood that if the angle is relatively small, then in the age range corresponding to the follow-up data of the target object, the target variation trend may be relatively close to the reference variation trend, and the condition of the organ or tissue of the target object may be relatively normal. If the angle is relatively large, then the organ or tissue of the target object may be at a relatively high risk. In some embodiments, the risk of the organ or tissue of the target object may be quantified according to a value of the angle. For example, if the angle is 0°, the risk of the organ or tissue of the target object may be relatively low. If the angle is closer to 90°, the risk of the organ or tissue of the target object may be relatively high (e.g., the highest). For example, if the reference variation trend goes down and the target variation trend goes down more sharply than the reference variation trend, the risk of the organ or tissue of the target object may be relatively high.

In some embodiments, the reference variation trend may go down, and the target variation trend may go up (e.g., after treatment). For example, the target line may be above the reference line. If the angle is relatively small, then in the age range corresponding to the follow-up data of the target object, the target variation trend may be relatively close to the reference variation trend, and the condition of the organ or tissue of the target object may be relatively normal. If the angle is relatively large, then the organ or tissue of the target object may be at a relatively good status.

It should be understood that the above description of some embodiments for determining the condition of the organ or tissue of the target object according to the target variation trend of the morphological characteristic values of the first target regions corresponding to the target object is merely provided for the purposes of illustration, and are not intended to limit the present disclosure. In some embodiments, target variation trends of the morphological characteristic values of other target regions corresponding to other sub-regions of the organ or tissue of the target object may be determined, and/or compared with corresponding reference variation trends. In some embodiments, the condition of the organ or tissue of the target object may be comprehensively assessed based on the target variation trend corresponding to each target region.

Figure 12:
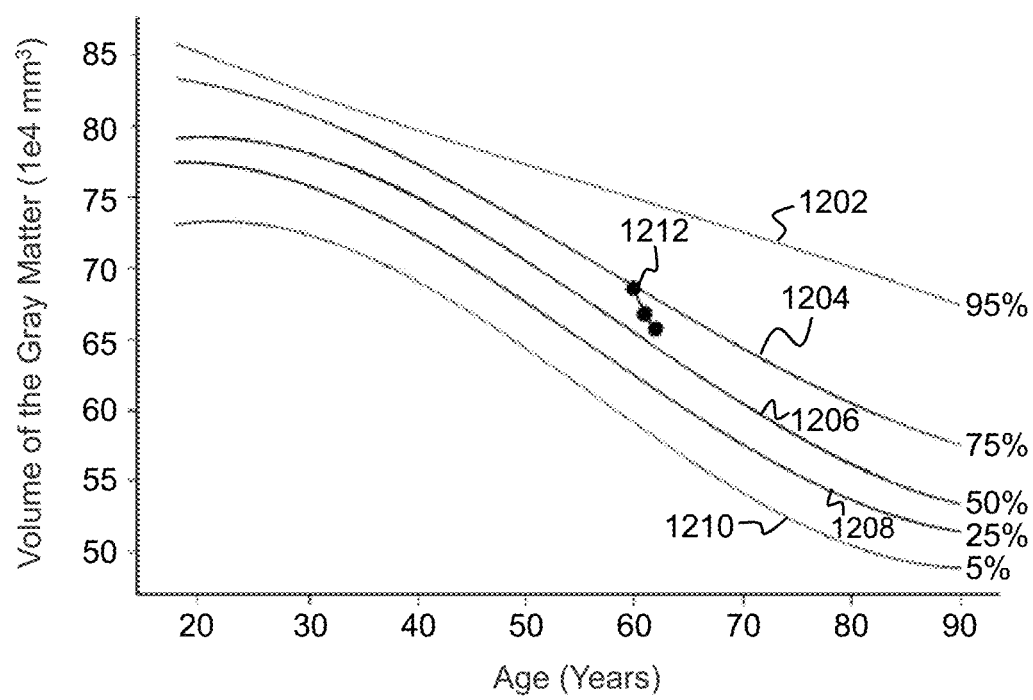
FIG. 12 is a schematic diagram illustrating an exemplary target variation trend of the gray matter volume of the brain of a target object and exemplary reference variation trends according to some embodiments of the present disclosure.
Figure 14:
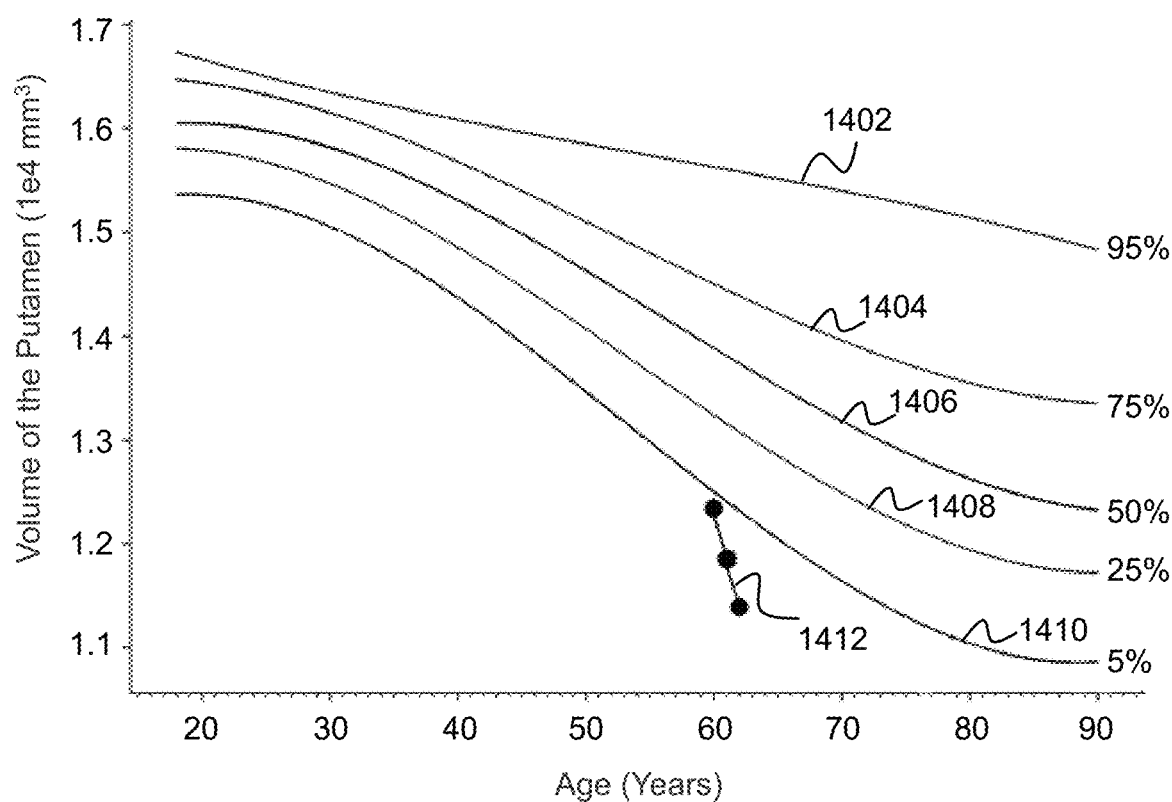
FIG. 14 is a schematic diagram illustrating an exemplary target variation trend of the putamen volume of the brain of a target object and exemplary reference variation trends according to some embodiments of the present disclosure.

FIGS. 12-14 are schematic diagrams illustrating exemplary target variation trends of a plurality of sub-regions of the brain of a target object and reference variation trends according to some embodiments of the present disclosure. Brain images of the target object may be collected at the age of 60 years old, 61 years old, and 62 years old to obtain follow-up data.

FIG. 12 is a schematic diagram illustrating an exemplary target variation trend of the gray matter volume of the brain of a target object and exemplary reference variation trends according to some embodiments of the present disclosure. In FIG. 12, age is used as the abscissa, and the gray matter volume is used as the ordinate. As shown in FIG. 12, curves 1202, 1204, 1206, 1208, and 1210 are fitted according to sample images, and represent reference variation trends of a 95th percentile value, a 75th percentile value, a 50th percentile value, a 25th percentile value, and a 5th percentile value of the gray matter volume, respectively. Curve 1212 represents a target variation trend of the gray matter volume of the brain of the target object from 60 to 62 years old. Three points on the curve 1212 may indicate the gray matter volume of the target object at 60, 61, and 62 years old, respectively.

FIG. 13 is a schematic diagram illustrating an exemplary target variation trend of the white matter volume of the brain of a target object and exemplary reference variation trends according to some embodiments of the present disclosure. In FIG. 13, age is used as the abscissa, and the white matter volume is used as the ordinate. As shown in FIG. 13, curves 1302, 1304, 1306, 1308 and 1310 are fitted according to sample images, and represent reference variation trends of a 95th percentile value, a 75th percentile value, a 50th percentile value, a 25th percentile value, and a 5th percentile value of the white matter volume, respectively. Curve 1312 represents a target variation trend of the white matter volume of the brain of the target object from 60 to 62 years old. The three points on the curve 1312 may indicate the white matter volume of the target object at 60, 61, and 62 years old, respectively.

FIG. 14 is a schematic diagram illustrating an exemplary target variation trend of the putamen volume of the brain of a target object and exemplary reference variation trends according to some embodiments of the present disclosure. In FIG. 14, age is used as the abscissa, and the putamen volume is used as the ordinate. As shown in FIG. 14, curves 1402, 1404, 1406, 1408 and 1410 are fitted according to sample images, and represent reference variation trends of a 95th percentile value, a 75th percentile value, a 50th percentile value, a 25th percentile value, and a 5th percentile value of the putamen volume, respectively. Curve 1412 represents a target variation trend of the putamen volume of the brain of the target object from 60 to 62 years old. The three points on the curve 1412 may indicate the putamen volume of the target object at 60, 61, and 62 years old, respectively.

As illustrated in FIGS. 12-14, volume reduction rates of the gray matter, the white matter, and the putamen in the brain of the target object are significantly greater than volume reduction rates of the three sub-regions of the brain of normal people, respectively. Specifically, volume reduction rates of the gray matter, the white matter, and the putamen in the brain of the target object are compared with volume reduction rates of the three sub-regions of the brain of normal people corresponding to certain percentile values, respectively. In some embodiments, the certain percentile value may correspond to an age when the follow-up data is first collected. For example, the volume reduction rate of the gray matter associated with the target object is compared with the volume reduction rate of the gray matter associated with normal people corresponding to the 75th percentile value as shown in FIG. 12. As another example, the volume reduction rate of the white matter associated with the target object is compared with the volume reduction rate of the white matter associated with normal people corresponding to the 75th percentile value as shown in FIG. 13. As a further example, the volume reduction rate of the putamen associated with the target object is compared with the volume reduction rate of the putamen associated with normal people corresponding to the 5th percentile value as shown in FIG. 14. Percentile values of the putamen volume of the target object at 60, 61, and 62 years old are less than 5%, which indicates that the putamen volume of the target object is obviously less than that of sample objects of the same age as the target object, and the risk of the brain atrophy of the target object is relatively high.

Figure 15:
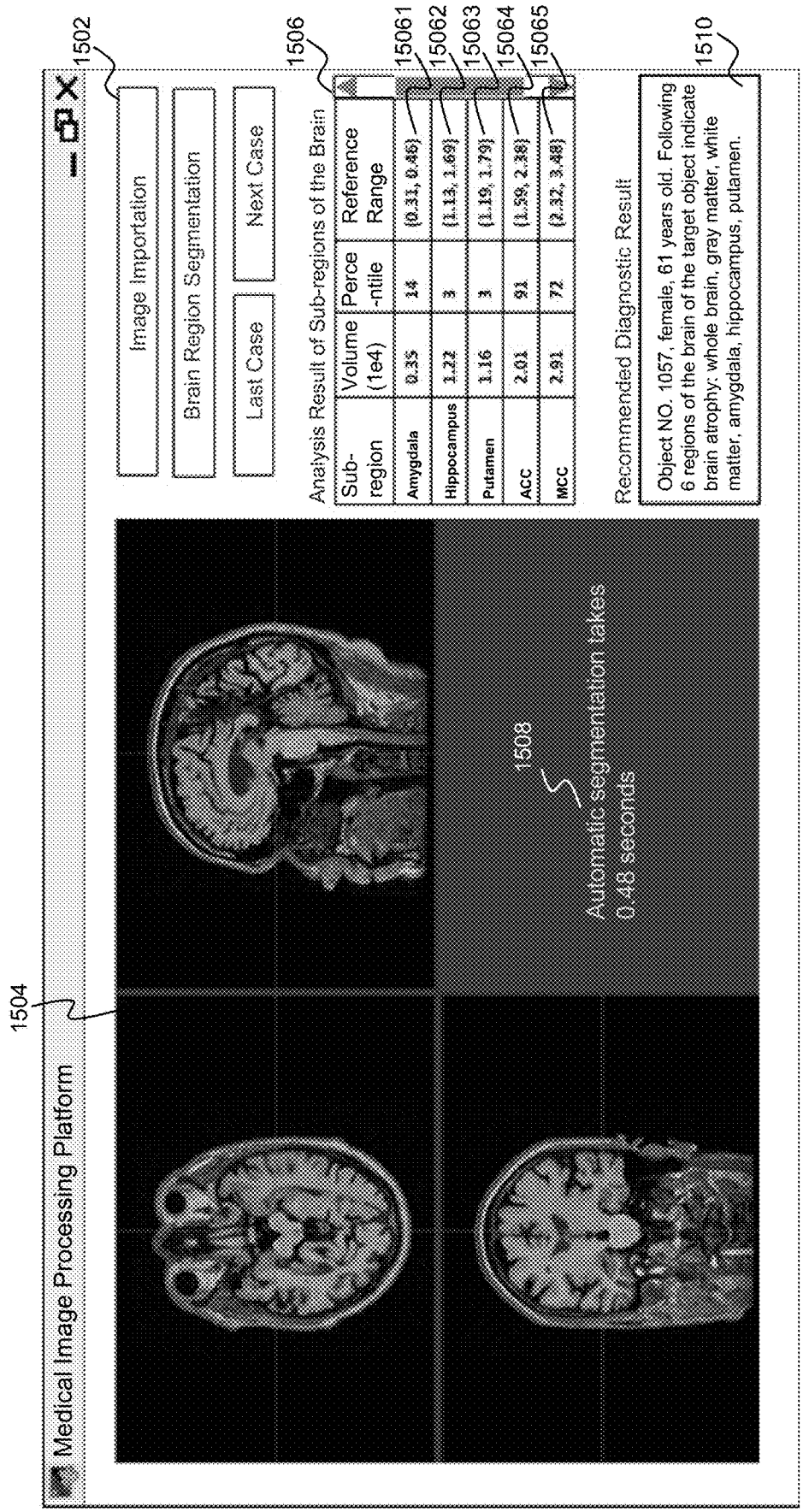
FIGS. 15 and 16 are schematic diagrams of exemplary medical image processing application interfaces according to some embodiments of the present disclosure.
Figure 16:
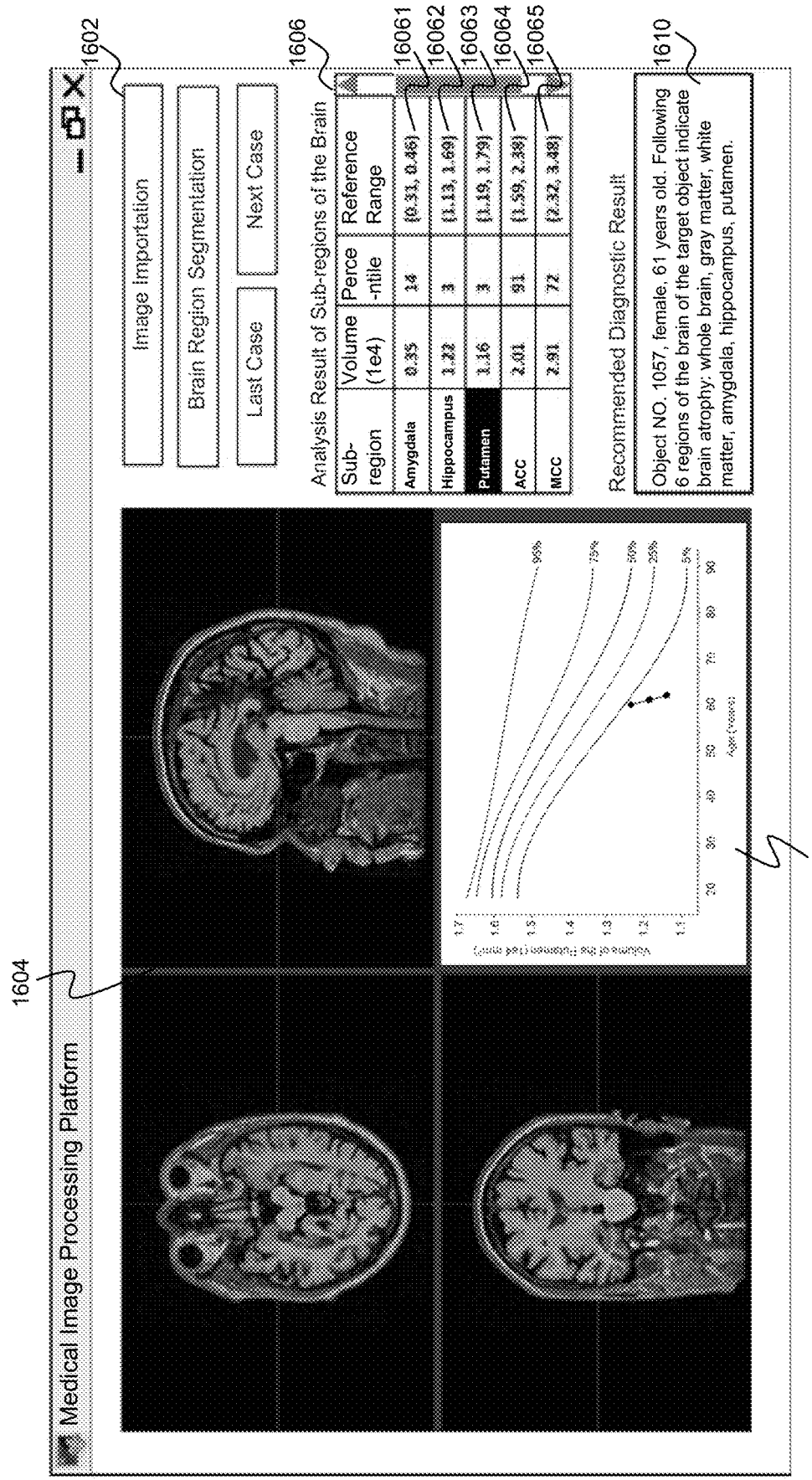

FIGS. 15 and 16 are schematic diagrams of exemplary medical image processing application interfaces according to some embodiments of the present disclosure.

At least part of functions of the present disclosure may be implemented by software. As shown in FIG. 15 (and/or FIG. 16), in some embodiments, the interface may include a control area 1502 (or 1602). A user (e.g., a doctor) may import a set of target data of an organ or tissue of a target object, or follow-up data including a plurality of sets of target data into the software, e.g., by clicking a relevant button (e.g., an "Image Importation" button) in the control area 1502 (or 1602). The user may also control the software to analyze the imported data by clicking a relevant button (e.g., a "Brain Region Segmentation" button) in the control area 1502 (or 1602). In some embodiments, the interface may further include a segmentation result display area 1504 (or 1604) for displaying a segmentation result of the organ or tissue of the target object (such as a brain sub-region segmented from the brain image). As shown in FIG. 15, in some embodiments, the segmentation result display area 1504 may include a sub-area 1508 to display image segmentation time consumption information. As shown in FIG. 16, in some embodiments, if data imported in the software is the follow-up data of the target object, the user may click an analysis result of a sub-region (such as an analysis result of "putamen") on an analysis result display area 1606. A sub-area 1608 of the segmentation result display area 1604 may then display a comparison of a target variation trend of morphological characteristic values of a sub-region of the target object and reference variation trends of percentile values of morphological characteristic values of the sub-region of sample objects. The diagram shown in the sub-area 1608 may be similar to the diagrams shown in FIGS. 12-14.

In some embodiments, the interface may further present an analysis result display area 1506 (or 1606) for displaying an analysis result of at least one sub-region of the organ or tissue of the target object. The analysis result of each sub-region may include the name of the sub-region, a morphological characteristic value of the sub-region of the target object, a reference range of the morphological characteristic value of the sub-region, a percentile value of the morphological characteristic value of the sub-region of the target object among morphological characteristic values of the sub-region of sample objects of the same age as the target object, etc. In some embodiments, the reference range may be determined based on morphological characteristic values of the sub-region of the organ or tissue of one or more normal sample objects (e.g., normal people). For example, the reference range may be fitted out based on morphological characteristic values of the sub-region of the organ or tissue of one or more normal sample objects.

In some embodiments, the analysis result display area 1506 (or 1606) may display sub-regions with different risk degrees differentially. For example, the sub-regions with different risk degrees may be displayed in different colors, different fonts, and/or different highlights. It may be understood that although FIGS. 15 and 16 are presented in black and white, the actual interface may be presented in color. In some embodiments, the analysis result of a high-risk sub-region may be displayed in a first color, the analysis result of a medium-risk sub-region may be displayed in a second color, and the analysis result of a low-risk sub-region may be displayed in a third color. For example, if percentile values of the hippocampus volume and the putamen volume of the target object are less than 5%, then the hippocampus and the putamen may be considered as high-risk sub-regions. The hippocampus analysis result 15062 (or 16062) and the putamen analysis result 15063 (or 16063) may be displayed in red. If the percentile value of the amygdala volume of the target object is between 5% and 25%, then the amygdala may be considered as a medium risk sub-region. The amygdala analysis result 15061 (or 16061) may be displayed in yellow. If percentile values of the anterior cingulate cortex volume and the middle cingulate cortex volume of the target object are larger than 25%, then the anterior cingulate cortex and the middle cingulate cortex may be considered as low-risk sub-regions. The anterior cingulate cortex (ACC) analysis result 15064 (or 16064) and the middle cingulate cortex (MCC) analysis result 15065 (or 16065) may be displayed in white. By displaying the sub-regions differentially, the user (e.g., a doctor) may be prompted to pay attention to abnormal sub-region(s).

In some embodiments, the interface may further present a recommended diagnostic result display area 1510 (or 1610) for displaying a recommended diagnostic result. The recommended diagnostic result may be automatically generated by the software according to the analysis result of each sub-region. In some embodiments, the user may make a diagnostic report with reference to the recommended diagnostic result. For example, the user may copy and paste the text in the recommended diagnostic result display area 1510 (or 1610) into a final diagnostic report (see, e.g., FIG. 17). Alternatively, the user may click a corresponding button to import the text into the final diagnostic report.

It should be noted that the above descriptions regarding the medical image processing application interfaces are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the medical image processing application interface may display any other information (e.g., a user name), and/or any other function (e.g., exporting the analysis result). In some embodiments, the information may be presented in various charts, diagrams, and/or graphs. For example, the analysis result display area 1606 may display the analysis result by a histogram instead of the table.

FIG. 17 is a schematic diagram of an exemplary diagnostic report according to some embodiments of the present disclosure.

In some embodiments, the diagnostic report may include object information 1702. The object information 1702 may include but not limited to a serial number (No.), a name, a gender, an age, a contact number, a diagnostician, an examination date, etc., of the target object.

In some embodiments, the diagnostic report may include an image segmentation result 1704 of the target object. The image segmentation result 1704 may include a transverse segmentation image, a coronal segmentation image, a sagittal segmentation image, or a combination thereof.

In some embodiments, the diagnostic report may include morphological characteristic information 1706 of an organ or tissue of the target object, including analysis result of at least one sub-region of the organ or tissue of the target object. The analysis result of each sub-region may include the name of the sub-region, a morphological characteristic value of the sub-region of the target object, a reference range of the morphological characteristic value of the sub-region, a percentile value of the morphological characteristic value of the sub-region of the target object among morphological characteristic values of the sub-region of sample objects of the same age as the target object, etc. In some embodiments, the diagnostic report may only display the analysis result of the sub-region(s) with relatively high risk.

In some embodiments, the diagnostic report may include one or more diagrams 1708 illustrating a comparison of a morphological characteristic value of at least one sub-region of the organ or tissue of the target object and that of normal people. In some embodiments, the diagnostic report may only display a diagram illustrating a comparison of a morphological characteristic value of a sub-region with a relatively high risk and that of normal people.

In some embodiments, the diagnostic report may further include a diagnostic result 1710. In some embodiments, the diagnostic result may include a recommended diagnostic result automatically generated by the image processing system 100. In some embodiments, the diagnostic report may be automatically generated by the image processing system 100. In some embodiments, at least part of the content of the diagnostic report may be manually inputted by a user. For example, the user may import at least one of the segmentation result display area 1504 (or 1604) in FIG. 15 (or FIG. 16) into the image segmentation result 1704 of the diagnostic report. As another example, the user may import a comparison result (shown in the sub-area 1608) of a high-risk sub-region of the target object and that of normal people into the diagram 1708. As another example, the user may import the analysis result of the high-risk sub-region of the target object in the analysis result display area 1506 (or 1606) in FIG. 15 (or FIG. 16) into the morphological characteristic information 1706. As another example, the user may copy and paste or import the text in the recommended diagnostic result display area 1510 (or 1610) in FIG. 15 (or FIG. 16) into the diagnostic result 1710 of the diagnostic report. Alternatively, the user may manually input a final diagnostic result with reference to the recommended diagnostic result.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the descriptions, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method implemented on at least one machine each of which has at least one processor and at least one storage device, the method comprising:
   obtaining a target image of a target object;
   determining a morphological characteristic value of a target region in the target image, the target region of the target image corresponding to a sub-region of an organ or tissue of the target object;
   determining, based on percentile values of morphological characteristic values of sample regions in a plurality of sample images of a plurality of sample objects, a target percentile value of the morphological characteristic value corresponding to the target object among morphological characteristic values corresponding to a first portion of the plurality of sample objects, wherein the first portion of the plurality of sample objects are of substantially same or similar age as the target object, and the sample regions correspond to the sub-region of the organ or tissue.

2. The method of claim 1, wherein the first portion of the plurality of sample objects are of a same gender as the target object.

3. The method of claim 1, wherein the morphological characteristic value includes at least one of a volume of the organ or tissue, a volume of the target region, a thickness of the target region, or a surface area of the target region.

4. The method of claim 1, wherein the organ or tissue includes a brain, and the morphological characteristic value includes at least one of a volume of the brain, a volume of the grey matter of the brain, a volume of the white matter of the brain, a volume of the putamen of the brain, a cortical thickness, or a cortex area.

5. The method of claim 1, wherein the determining the morphological characteristic value of the target region in the target image includes:

segmenting, using a target segmentation model, the target region from the target image, wherein the target segmentation model includes a target artificial intelligence model that is produced according to a process, the process including:
 obtaining a plurality of training images associated with a second sample organ or tissue of at least one second sample object, the second sample organ or tissue being of a same type as the organ or tissue of the target object;
 obtaining an initial artificial intelligence model; and
 determining the target artificial intelligence model by training the initial artificial intelligence model using the plurality of training images; and
determining the morphological characteristic value of the target region using one or more morphometry techniques.

6. The method of claim 1, further comprising:
ranking morphological characteristic values corresponding to the first portion of the plurality of sample objects in a descending order; and
determining, based on the ranking, percentile values of the morphological characteristic values corresponding to the first portion of the plurality of sample objects.

7. The method of claim 1, wherein the determining, based on the percentile values of the morphological characteristic values of the sample regions in the plurality of sample images of the plurality of sample objects, a target percentile value of the morphological characteristic value corresponding to the target object among the morphological characteristic values corresponding to the first portion of the plurality of sample objects includes:
 determining a relation of the morphological characteristic values corresponding to the plurality of sample objects and age of each of the plurality of samples object;
 determining, based on age of the target object, the morphological characteristic value corresponding to the target object, and the relation, the target percentile of the morphological characteristic value corresponding to the target object among the morphological characteristic values corresponding to the first portion of the plurality of sample images of the plurality of sample objects.

8. The method of claim 7, further comprising:
fitting out a curve representing the relation of the morphological characteristic values corresponding to the plurality of sample objects and the age of each of the plurality of samples object.

9. The method of claim 1, wherein the determining, based on the percentile values of the morphological characteristic values of the sample regions in the plurality of sample images of the plurality of sample objects, a target percentile value of the morphological characteristic value corresponding to the target object among the morphological characteristic values corresponding to the first portion of the plurality of sample objects includes:
 fitting out, based on the percentile values of the morphological characteristic values corresponding to the first portion of the plurality of sample objects and the morphological characteristic values corresponding to first portion of the plurality of sample objects, a second curve by using a morphological characteristic value as a dependent variable and using a percentile value as an independent variable; and
 determining, based on the second curve, the target percentile value of the morphological characteristic value corresponding to the target object among the morphological characteristic values corresponding to the first portion of the plurality of sample objects.

10. The method of claim 1, wherein the target percentile value of the morphological characteristic value corresponding to the target object is configured to access a condition of the organ or tissue of the target object.

11. A system, comprising:
at least one storage device storing a set of instructions; and
at least one processor in communication with the storage device, wherein when executing the set of instructions, the at least one processor is configured to cause the system to perform operations including:
 obtaining a target image of a target object;
 determining a morphological characteristic value of a target region in the target image, the target region of the target image corresponding to a sub-region of an organ or tissue of the target object;
 determining, based on percentile values of morphological characteristic values of sample regions in a plurality of sample images of a plurality of sample objects, a target percentile value of the morphological characteristic value corresponding to the target object among morphological characteristic values corresponding to a first portion of the plurality of sample objects for assessing a condition of the organ or tissue of the target object, wherein the first portion of the plurality of sample objects are of substantially same or similar age as the target object, and the sample regions correspond to the sub-region of the organ or tissue.

12. The system of claim 11, wherein the first portion of the plurality of sample objects are of a same gender as the target object.

13. The system of claim 11, wherein the morphological characteristic value includes at least one of a volume of the organ or tissue, a volume of the target region, a thickness of the target region, or a surface area of the target region.

14. The method of claim 11, wherein the organ or tissue includes a brain, and the morphological characteristic value includes at least one of a volume of the brain, a volume of the grey matter of the brain, a volume of the white matter of the brain, a volume of the putamen of the brain, a cortical thickness, or a cortex area.

15. The system of claim 11, wherein the determining the morphological characteristic value of the target region in the target image includes:
 segmenting, using a target segmentation model, the target region from the target image, wherein the target segmentation model includes a target artificial intelligence model that is produced according to a process, the process including:
  obtaining a plurality of training images associated with a second sample organ or tissue of at least one second sample object, the second sample organ or tissue being of a same type as the organ or tissue of the target object;
  obtaining an initial artificial intelligence model; and
  determining the target artificial intelligence model by training the initial artificial intelligence model using the plurality of training images; and
 determining the morphological characteristic value of the target region using one or more morphometry techniques.

16. The system of claim 11, further comprising:
ranking morphological characteristic values corresponding to the first portion of the plurality of sample objects in a descending order; and
determining, based on the ranking, percentile values of the morphological characteristic values corresponding to the first portion of the plurality of sample objects.

17. The system of claim 11, wherein the determining, based on the percentile values of the morphological characteristic values of the sample regions in the plurality of sample images of the plurality of sample objects, a target percentile value of the morphological characteristic value corresponding to the target object among the morphological characteristic values corresponding to the first portion of the plurality of sample objects includes:
determining a relation of the morphological characteristic values corresponding to the plurality of sample objects and age of each of the plurality of samples object;
determining, based on age of the target object, the morphological characteristic value corresponding to the target object, and the relation, the target percentile of the morphological characteristic value corresponding to the target object among the morphological characteristic values corresponding to the first portion of the plurality of sample images of the plurality of sample objects.

18. The system of claim 17, further comprising:
fitting out a curve representing the relation of the morphological characteristic values corresponding to the plurality of sample objects and the age of each of the plurality of samples object.

19. The system of claim 11, wherein the determining, based on the percentile values of the morphological characteristic values of the sample regions in the plurality of sample images of the plurality of sample objects, a target percentile value of the morphological characteristic value corresponding to the target object among the morphological characteristic values corresponding to the first portion of the plurality of sample objects includes:
fitting out, based on the percentile values of the morphological characteristic values corresponding to the first portion of the plurality of sample objects and the morphological characteristic values corresponding to first portion of the plurality of sample objects, a second curve by using a morphological characteristic value as a dependent variable and using a percentile value as an independent variable; and
determining, based on the second curve, the target percentile value of the morphological characteristic value corresponding to the target object among the morphological characteristic values corresponding to the first portion of the plurality of sample objects.

20. A non-transitory computer readable medium, comprising at least one set of instructions, wherein when executed by at least one processor of a computing device, the at least one set of instructions cause the at least one processor to effectuate a method comprising:
obtaining a target image of a target object;
determining a morphological characteristic value of a target region in the target image, the target region of the target image corresponding to a sub-region of an organ or tissue of the target object;
determining, based on percentile values of morphological characteristic values of sample regions in a plurality of sample images of a plurality of sample objects, a target percentile value of the morphological characteristic value corresponding to the target object among morphological characteristic values corresponding to a first portion of the plurality of sample objects for assessing a condition of the organ or tissue of the target object, wherein the first portion of the plurality of sample objects are of substantially same or similar age as the target object, and the sample regions correspond to the sub-region of the organ or tissue.

* * * * *